US012665074B1

(12) United States Patent
 Ward

(10) Patent No.: US 12,665,074 B1
(45) Date of Patent: Jun. 23, 2026

(54) SYSTEMS AND METHODS FOR PROVIDING VIRTUAL CARE

(71) Applicant: Dignity Health, San Francisco, CA (US)

(72) Inventor: Joel Ward, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 73 days.

(21) Appl. No.: 17/560,102

(22) Filed: Dec. 22, 2021

Related U.S. Application Data

(60) Provisional application No. 63/129,107, filed on Dec. 22, 2020.

(51) Int. Cl.
 *G16H 40/20* (2018.01)
 *G16H 40/67* (2018.01)
(52) U.S. Cl.
 CPC ............. *G16H 40/20* (2018.01); *G16H 40/67* (2018.01)

(58) Field of Classification Search
 CPC .............................. G16H 40/20; G16H 40/67
 See application file for complete search history.

(56) References Cited

U.S. PATENT DOCUMENTS

| | | | | |
|---|---|---|---|---|
| 2016/0246936 | A1* | 8/2016 | Kahn | ..................... G16H 80/00 |
| 2017/0032092 | A1* | 2/2017 | Mink | ................. G06Q 30/0241 |
| 2021/0020318 | A1* | 1/2021 | Movassaghi | ........... G16H 40/67 |

* cited by examiner

*Primary Examiner* — Rachelle L Reichert
(74) *Attorney, Agent, or Firm* — Polsinelli PC

(57) ABSTRACT

Disclosed herein are systems and methods for providing virtual care for a patient. In one implementation, a patient care session corresponding to care for a patient is automatically joined in response to a command to initiate the patient care session. The patient care session is automatically joined using a location identifier and a password. The patient care session is presented in a visit mode of a virtual care interface. The visit mode prevents access to functionality outside of the patient care session. The visit mode of the virtual care interface is automatically ended following a termination of the patient care session. The virtual care interface is presented in a locked state.

20 Claims, 18 Drawing Sheets

AUTOMATICALLY JOIN A PATIENT CARE SESSION
1602

PRESENT THE PATIENT CARE SESSION IN A VISIT MODE OF A VIRTUAL CARE INTERFACE
1604

AUTOMATICALLY END THE VISIT MODE OF THE VIRTUAL CARE INTERFACE
1606

PRESENT THE VIRTUAL CARE INTERFACE IN A LOCKED STATE
1608

1600

SYSTEMS AND METHODS FOR PROVIDING VIRTUAL CARE

CROSS-REFERENCE TO RELATED APPLICATIONS

The present application claims priority under 35 U.S.C. § 119 to U.S. Provisional Application No. 63/129,107, entitled "Systems and Methods For Providing Virtual Care" and filed Dec. 22, 2020, which is specifically incorporated by reference in its entirety herein.

TECHNICAL FIELD

Aspects of the present disclosure relate to patient management and healthcare delivery and more particularly to virtually integrated care delivery, remote patient monitoring, virtual patient observation, and virtual care coordination.

BACKGROUND

Many patients encounter various challenges in accessing and receiving healthcare. For example, many patients live in rural areas with inadequate access to primary healthcare. Additionally, the care of many patients involves specialized care, with those having expertise in the relevant specialties being at disparate locations. These challenges are exacerbated in situations where the patient is being held in quarantine isolation. For example, when the patient has or is suspected to have a highly communicable disease, direct contact with the patient may be limited, particularly in situations where access to personalized protection equipment is limited. In such situations, providing care, facilitating patient visits, and coordinating access to specialists can be difficult. It is with these observations in mind, among others, that various aspects of the present disclosure were conceived and developed.

SUMMARY

Implementations described and claimed herein address the foregoing problems by providing systems and methods for virtual care for a patient. In one implementation, a patient care session corresponding to care for a patient is automatically joined in response to a command to initiate the patient care session. The patient care session is automatically joined using a location identifier and a password. The patient care session is presented in a visit mode of a virtual care interface. The visit mode prevents access to functionality outside of the patient care session. The visit mode of the virtual care interface is automatically ended following a termination of the patient care session. The virtual care interface is presented in a locked state.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

DETAILED DESCRIPTION

Figure 1:
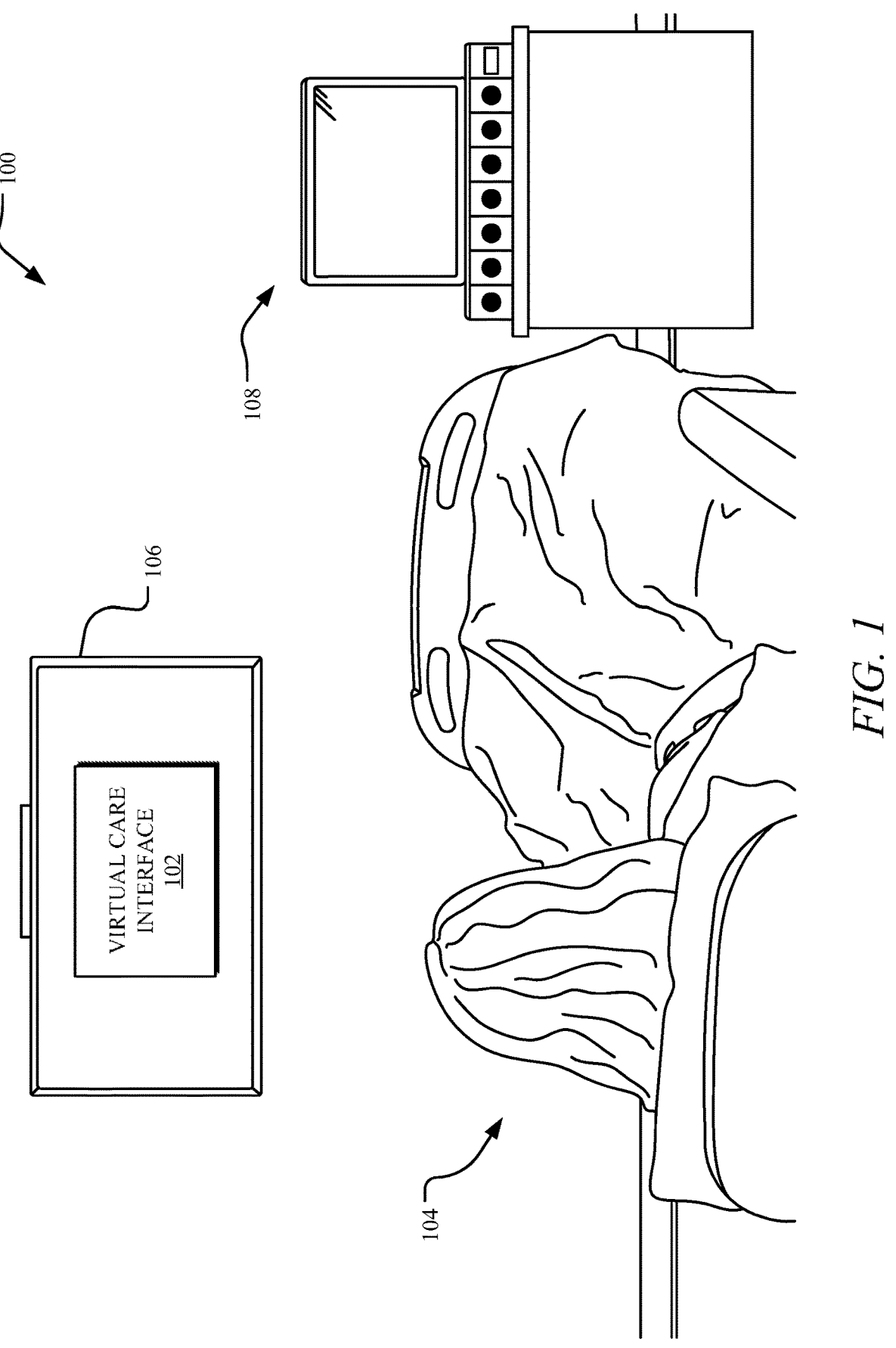
FIG. 1 illustrates an example system for providing virtually integrated care for a patient.

Aspects of the present disclosure involve systems and methods for providing virtual care. Interaction with one or more patients is facilitated by combining multiple modalities of care into a single digital healthcare platform. The platform is accessible in environments including, without limitation, hospital, nursing home, clinical, remote, outpatient, assisted living, home, quarantine, and/or the like. Generally, multiple healthcare services may be provided across the spectrum of care independent of location. Conventional telemedicine visits typically involve an expensive telemedicine cart used for multiple patient rooms with a practitioner physically moving the cart across the rooms under isolation conditions. As such, the practitioner is forced to spend time moving the telemedicine cart between rooms, rather than providing care to other patients and decreasing the availability of personal protection equipment. Accordingly, the presently disclosed technology provides a single platform of independent healthcare features for use across all aspects of healthcare and patient locations utilizing user devices associated with patients, providers, and a virtual care coordinator. The platform includes video communication facilitating a broad scope of virtual access. A virtual care visit may be initiated without user interaction with the interface. Instead, the virtual care visit may be initiated by the virtual care coordinator. As such, care may be delivered directly to a patient independent of the presence of provider personnel, such as a bedside nurse.

Generally, the presently disclosed technology includes a virtual care system providing virtual visits and examinations for one or more patients. The virtual care system provides a user friendly patient interface facilitating virtual care through a virtual care coordinator. The interface includes a video examination and visit system for communication and/or examination. The video examination and visit system may be used to conduct patient examinations, health related visits, social visits, and/or the like. The interface further includes an integrated web browser and media player for accessing and interacting with online resources and other care resources, such as educational videos and content. The access and interaction may be directed by the virtual care coordinator. Overall, the virtual care system integrates multiple virtual care functions, including, but not limited to, virtual visits, virtual examination, virtual patient sitting, virtual patient observation, virtual patient education, remote home monitoring and care, and/or the like.

In one aspect, the virtual care system providing a virtual care interface using one or more patient systems in communication with a virtual coordinator system over a network. The patient systems interact with the virtual coordinator system using a communications manager, such as a cloud based messaging service where messages sent between the systems include instructions for execution by the virtual care interface for performing one or more functions. The functions may include, without limitation, video communication functionality in connection with care visits, presenting messages and other communications, call light management, media streaming, media access and interaction, online resource access and interaction, patient medical information management, and/or the like. For example, the video communication functionality may include camera controls, peripheral device control, screen sharing, and microphone and volume control, among other video platform functionality. The virtual care interface may display one or more messages to a patient, such as appointment times, scheduling, and/or messages from a virtual care coordinator, provider, or other users. Media may be streamed via the virtual care interface from various sources, including local or cloud storage, and online content may be provided through an integrated web browser, as directed by the virtual coordinator system. The virtual care interface may automatically or manually capture patient vital signs and wellness. For example, the patient may provide a wellness score on a scale (e.g., 1-5) corresponding to how the patient feels subjectively. The virtual care system provides robust patient care for patients that are in remote locations, quarantined, or disposed in other environments by combining multiple modalities of care into a single digital healthcare platform.

The presently disclosed technology improves healthcare delivery by providing a platform that facilitates patient care and management independent of location or condition of the patient or provider. Accordingly, the virtual care system decreases the use of and need for personal protective equipment in connection with the care of quarantined or otherwise isolated patients, while providing enhanced care through access to specialized medical services in disparate locations and facilitating examination and social visits with such patients. In addition to virtual healthcare management of cohorted quarantined patients, the virtual care system provides: telemedicine between environments, such as hospitals, clinics, institutions, schools, etc.; virtual nursing and healthcare coordination; virtual provider visits and examinations; virtual patient observation and sitting; remote patient monitoring at facilities or home; virtual referrals between facilities; virtual coordination of care independent of location of receiving or origination service; virtual nursing; patient centered coordination of ancillary services; patient education; patient engagement and support using resources, such as appointment scheduling, support groups, room service, etc.; virtual patient observation for monitoring of falls; patient messaging, patient call light management; virtual social and ancillary visits; and/or the like.

Figure 2:
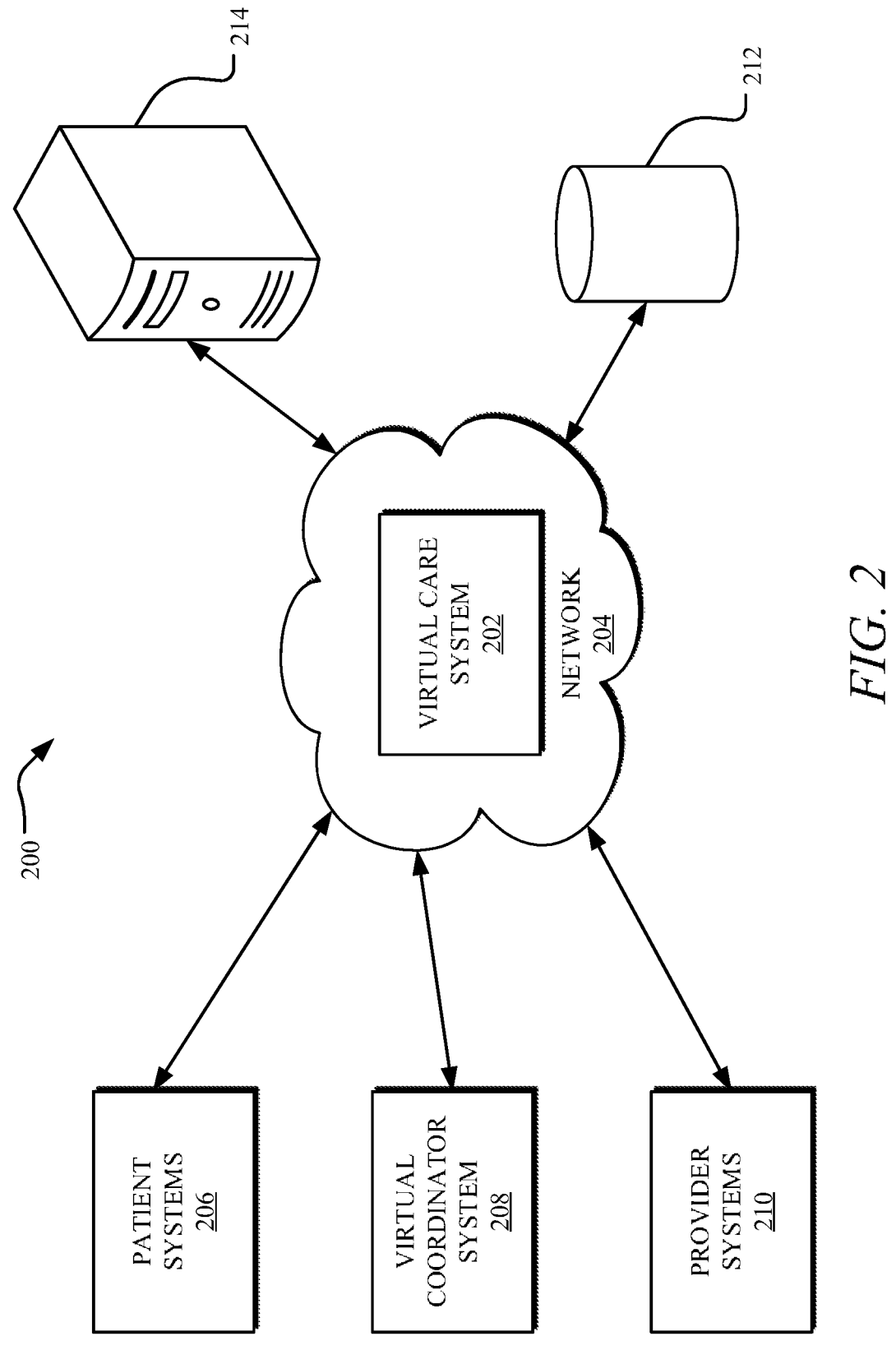
FIG. 2 shows an example network environment for managing virtual care delivery.

To begin a detailed description of an example system 100 including a virtual care interface 102 of a virtual care system 202 for providing virtually integrated care delivery for a patient 104, reference is made to FIGS. 1-2. The virtual care interface 102 facilitates communication and interaction among a patient environment, a virtual coordinator environment, one or more provider environments, and other environments in connection with healthcare delivery and management.

The patient environment may be any environment in which the patient 104 is located and/or receiving care. For example, the patient environment may be a patient room in a hospital where the patient 104 is receiving care and in some cases quarantined due to a nature of a condition of the patient 104. It will be appreciated that the patient environment may correspond to other home, remote, or facility locations. Similarly, the provider environment may correspond to any environment where a provider is located and/or any environment from which care or healthcare resources are provided. The provider environments may be disparate locations. For example, a team of providers, including advanced care nurses, unit-based registered nurses, licensed practical nurses, certified nursing assistants, hospitalists, specialty physicians, primary physicians, and/or the like may provide coordinated care for the patient 104 from various locations using the virtual care interface 102. The virtual coordinator environment may correspond to a control center directing or otherwise coordinating various aspects of the virtual care interface 102. A virtual care coordinator may be deployed in the virtual coordinator environment. In one example, the virtual coordinator environment is a command center of the hospital where the patient 104 is receiving care, but it will be appreciated that the virtual coordinator environment may be various locations. The other environments may correspond to various locations associated with other personnel and resources involved in providing care to the patient 104, including, without limitation, social workers, case managers who coordinate patient care, other caregivers, other patients, family members, support groups, food delivery, ancillary services, and/or the like. As such, the virtual care interface 102 provides multiple healthcare services across the spectrum of care independent of location of the various people involved.

The system 100 may be deployed in a network environment 200 in which patient care delivery is managed using a virtual care system 202. The virtual care interface 102 may be generated by the virtual care system 202. Users may access and interact with the virtual care system 202 over a network 204 with one or more user devices, computing devices, input devices, and output devices associated with the network environment 200. Such devices may form, be integrated with, or otherwise be associated with one or more patient systems 206, a virtual coordinator system 208, and one or more provider systems 210. The patient systems 206 may each be associated with a patient environment, the virtual coordinator system 208 may be associated with the virtual coordinator environment, and the provider systems 210 may each be associated with a provider environment. Additional personnel in the other environments may access the virtual care system 202 using a user device.

The virtual care interface 102 may be presented in various manners using a variety of input and output devices of the patient system 206, as described herein and configured for various forms input and output, including visual, audio, tactile, and/or the like. For example, the input and output devices may include, one or more cameras, one or more displays, one or more microphones, one or more speakers, one or more projectors, and/or the like. It will be appreciated that such features may be provided as one device or multiple devices in communication. In one implementation, the virtual care interface 102 is presented with a patient device 106 associated with the patient system 206 including a tactile touch-screen display (e.g., a tablet or touch-screen monitor) configured to receive tactile input from one or more users, such as the patient 104 and any other users in the patient environment, and display visual output. The patient device 106 may further be configured to receive visual input in the form of gesture commands, audio input in the form of voice commands, and other tactile input. The patient system 206 may include peripheral devices 108 in communication with the patient device 106. The peripheral devices 108 may include various medical devices configured to capture patient medical information for the patient 104.

In some implementations, the virtual care interface 102 may be controlled via voice recognition using activation keywords or phrases. For example, a microphone may be used to receive audio, process the audio, and provide appropriate inputs to control the patient device 106.

A patient device (e.g., a monitor or television) may include a communication port that allows inputs to be provided to the patient device for controlling various features. For example, a television may receive serial control communication from a port that can turn on/off, change volume, or change the input of the television. Codes specific to a type of television may be used to control the television. Using the communication port, a virtual team may ask permission to take over the television if there is a separate computer for initial communication like a smaller bedside tablet. In some cases, a computer (e.g., a computer without a screen) may be used to listen for an activation phrase, which may be customized. Using the communication port, the computer may turn the television on and switch the television's input so the patient can see and talk with the virtual team. After the patient care session, the virtual team can ask the patient whether they prefer to leave the television on (and switch back the input) or turn the television off. In some cases, upon the termination of the patient care session, the communication port may be used to automatically turn off the television or return the television back to the state the television was in prior to the patient care session. For example, the computer may store the state of the television prior to the patient care session, allowing the computer to set the computer back to the same state upon termination of the patient care session.

In one implementation, the virtual care interface 102 is presented with the patient device 106 for interaction with the patient 104 and any users in the patient environment, such as a nurse or other provider. The virtual care interface 102 may be displayed on a display of the patient device 106 in a locked state or an unlocked state controlled by an access restriction system of the virtual care system. In one implementation, the virtual care system 202 prevents the patient device 106 from initiating any functions due to inactivity, such as initiating a screen saver, turning off, transitioning into sleep mode, and/or the like. However, if a problem is detected, the patient device 106 may be automatically restarted. Additionally, the virtual care interface 102 may be transitioned into a night mode to encourage rest and sleep for the patient 104.

The access restriction system ensures the virtual care interface 102 is consistently accessible in either a locked state or unlocked state. In one implementation, the access restriction system prevents access to other systems and functions of the patient device 106 outside of the virtual care interface 102. When the virtual care interface 102 is in the locked state, functionality and information are displayed and accessible, with the access restriction system preventing any further access to the patient device 106 beyond the restricted interface. When the virtual care interface 102 is in the unlocked state, additional functionality of the patient device 106 is accessible. In one example, the virtual care interface 102 remains in the locked state for interaction with the patient 104, and the virtual care interface 102 may be transitioned into the unlocked state by a provider for additional access and functionality.

In one implementation, the virtual care interface 102 is presented as a continuous layer and intercepts any input in the locked state. For example, where the virtual care interface 102 is presented using a display of the patient device 106, the virtual care interface 102 may be presented as a continuous layer across an entirety of the display. Any input captured using an input device of the patient device 106, such as touch input captured using a touchscreen, voice input, visual input, input provided via a mouse, keyboard, or similar device, and/or the like is intercepted by the virtual care interface 102, thereby preventing access to the patient device 106 beyond the virtual care interface 102. Upon receiving input using an input device of the patient device 106, the virtual care system 202 captures the input before the input is obtained by aspects of the patient device 106 outside of the virtual care interface 102 and determines whether the input corresponds to permitted functionality of the virtual care interface 102. If the input corresponds to permitted functionality of the virtual care interface 102, the input is processed by the virtual care system. If the input corresponds to functionality outside the virtual care interface 102, the input is rejected.

The access restriction system may transition the virtual care interface 102 from the locked state to the unlocked state upon receipt of an authenticated command. In one implementation, input is captured using one or more input devices of the patient device 106. The input may be tactile input captured using a touchscreen, voice input captured using one or more microphones, visual input captured using one or more cameras, and/or other input. For example, the tactile input may include a touch pattern, touch motion, or code input via touch (e.g., using a digital keyboard or text pad). The voice input may include a voice command or voice recognition of an authorized user, and the visual input may include a gesture command, facial recognition, or other visual recognition (e.g., scanning a user identification card, QR code, optical code, etc.). Other input may include communications exchanged between one or more devices with the patient device 106. For example, an authenticated user device associated with an authorized individual may exchange messages, such as an encrypted passcode or other communication, with the patient device 106. In some cases, the user device may be paired with the patient device 106 to facilitate communication exchange. In another example, a code may be input using a keyboard or other input device. Overall, the virtual care system 202 and/or the patient device 106 may include a library of authentication profiles. The input is compared with the authentication profiles to validate the input. If the input is validated as an authenticated command, the access restriction system transitions the virtual care interface 102 from the locked state to the unlocked state.

In one implementation, the virtual care interface 102 is transitioned to the unlocked state using a touch pattern. A touchscreen of the patient device 106 detects a series of touches in a pattern. For example, the series of touches may be made in a sequential order and corresponding to a set of rectangles. In another example, the series of touches is made in an order corresponding to corners of the touchscreen (e.g., a first corner, second corner, third corner, and fourth corner). The touch pattern is authenticated against a corresponding authentication profile. If the touch pattern matches the authentication profile, the touch pattern is validated as an authenticated command and the virtual care interface 102 transitions to the unlocked state.

The unlocked state of the virtual care interface 102 may similarly include a continuous layer across an entirety of the display, while permitting additional functionality. In the unlocked state, the virtual care interface 102 may permit additional input to pass through to the patient device 106 without intercepting it. In this case, the virtual care interface 102 may still block access to a portion of the functionality of the patient device 106, while providing additional access commensurate with a privilege level of an authenticated user. For example, a technician may enter an authenticated command transitioning the virtual care interface 102 into an unlocked state where the technician is able to access aspects of the patient device 106 for software updates, troubleshooting, and maintenance. Following action by the technician, the virtual care interface 102 automatically or manually transitions from the unlocked state to the locked state. In another example, the authenticated user is a provider, such as a nurse, having a privilege level that provides access to additional functionality, such as control of and communication with one or more peripheral devices 108, as well as access to other resources for the patient 104.

When the virtual care interface 102 is in the unlocked state, it may send a notification to the virtual coordinator system 208. The virtual coordinator system 208 maintains a list of which of the patient systems 206 are connected (in the locked state) and which are disconnected (in the unlocked state or otherwise unavailable). Upon receiving the message from the virtual care interface 102 corresponding to the patient device 106 transitioning from the locked state to the unlocked state, the virtual coordinator system 206 removes the patient device 106 from the list of connected devices. The virtual coordinator system 206 automatically detects whether the patient device 106 is connected at predetermined intervals (e.g., every ten seconds). If the patient device 106 is removed from the list of connected devices unexpectedly or for longer than a predetermined threshold (e.g., because the patient device 106 has no power), the virtual coordinator system 208 may flag the patient device 106 for follow up or analysis by a technician. In one implementation, the virtual care interface 102 automatically transitions from the unlocked state into the locked state after a predetermined amount of time.

In one implementation, the virtual care interface 102 remains in the locked state for interaction with the patient 104. The locked state of the virtual care interface 102 includes a set of restricted access functions, including a call light, a wellness check-in, messaging, and/or the like. Various combinations of the restricted access functions may be provided based on a care access mode, which may include a hospital mode, assisted living mode, home mode, remote mode, night mode, pre-procedure mode, post-procedure mode, and/or the like. The call light may be used to call the virtual care coordinator. In some implementations, the virtual care interface 102 may be integrated with the hospital or medical facility call light system.

The wellness check-in may be used for the patient 104 to provide regular updates about the subjective condition of the patient 104. For example, the wellness check-in may include a scale reflecting how the patient 104 is feeling. The scale may include a range of numbers, a spectrum of graphically depicted emotions, and/or the like. The wellness check-in may further include vitals of the patient 104 that are manually or automatically captured. For example, the vitals may be captured using the peripheral devices 108, which may include wearables worn by the patient 104 or other medical devices, sensors, and instruments. The peripheral devices 108 may be in communication with the patient device 106, such that the patient device 106 automatically obtains the vitals according to access levels granted by the patient 104. The wellness check-in is sent from the patient device 106 to the virtual care coordinator via the virtual care interface 102. The messaging may receive, present, and exchange communications between the patient 104, the virtual care coordinator, one or more providers, and/or other personnel associated with the patient 104.

In addition to the restricted access functions, the virtual care interface 102 awaits commands from the virtual coordinator system 208 associated with the virtual care coordinator. As described in more detail here, the virtual care coordinator may be a nurse, a virtual nurse generated using artificial intelligence, or a combination thereof. The command may include initiation of a patient care session, such as a patient examination or a patient visit (e.g., a social visit). The patient care session may include a video connection with associated functionality. In one implementation, the virtual care interface 102 receives a command to initiate the patient care session and receives a Uniform Resource Locator (URL) or other web resource that specifies a location on a computer network and a mechanism for retrieving the web resource. A password and identifier associated with the patient device 106 are obtained in connection with the patient care session. The identifier may be customized as a name, room, and/or the like to identify the users associated with the patient care session. The virtual care system 202 captures a patient identifier associated with the patient 104 and/or the patient device 106 and renames the identifier joining the patient care session using the patient identifier. Using the address and the patient identifier, the patient care session is initiated.

In connection with initiation of the patient care session, the access restriction system transitions the virtual care interface 102 into a visit mode. In the visit mode, access to functionality outside of the patient care session is prevented. Stated differently, the continuous layer of the virtual care interface 102 becomes transparent to present the patient care session, while continuing to intercept input uncorrelated with the patient care session.

In one implementation, the patient care session may be initiated from the patient device 106 or configured when the virtual care interface 102 is in the unlocked state. In the unlocked state, an access panel of the virtual care interface 102 may be presented. The access panel includes fields for entering an identifier associated with the patient device 106 and/or the patient 104 and a location identifier. Using this information, the virtual care system 202 may be configured for video connection during the patient care session. A patient care session may be initiated by the virtual coordination system or other devices when the virtual care interface 102 is in the locked state or unlocked state and by the patient device 106 when the virtual care interface 102 is in the unlocked state.

Upon receiving a command to initiate a patient care session, the virtual care interface 102 automatically executes a login procedure for joining the patient care session via the patient device 106. Automatic execution of the login procedure may be triggered by the virtual coordinator system 208, the patient system 206, the provider system 210, and/or other user devices of the virtual care system. In one implementation, the virtual care interface 102 issues a command to open a browser and automatically input a care session locator, such as a URL or other web resource, to navigate to a patient care session site providing video conferencing and related services. The care session locator corresponds to a patient care session involving the patient 104 and one or more participants involved with patient care delivery, such as providers, social workers, case managers who coordinate patient care, other caregivers, other patients, family members, friends, users involved in support groups, users providing food delivery or services, uses providing ancillary services, and/or the like. The care session locator may launch a video conferencing application. The video conferencing application may be a separate application launched by and controlled using the virtual care interface 102. Alternatively, the video conferencing application may be integrated into and part of the virtual care interface 102. A passcode associated with the patient care session and a patient identifier may be automatically input to join the patient care session using the patient device 106. In one implementation, once the patient care session is joined, the virtual care interface 102 closes the browser and transitions into the visit mode, preventing access to functionality outside of the patient care session.

Input corresponding to the patient care session may be captured using one or more input devices associated with the patient 104, the virtual care coordinator, and/or other users. In one implementation, the input is obtained by the virtual care interface 102 and redirected to the video conferencing application, which may execute one or more commands associated with the patient care session based on the input. The virtual care interface 102 may redirect input to the video conferencing application based on a privilege level. For example, the virtual care interface 102 may prevent any input from the patient device 106 or in some cases limit the input that is accepted to the virtual coordinator system 208 or the provider systems 210. The input may be used to control various functions or other aspects of the patient care session presented using the video conferencing application, including, but not limited to, audio control, video control, resource sharing, participant management, messaging, transfer control, meeting control, accessibility control, and/or the like.

Audio control may include muting, unmuting, volume control, audio input and output sources, and/or the like to one or more participants. Similarly, video control may include starting video, stopping video, display settings, video capture or recording settings, and/or the like. Resource sharing may include screen sharing by one or more participants, media sharing, and/or the like. Participant management may include adding or removing participants, audio or video control of selected participants, notifications regarding participants, display settings related to participants, management of participant controls, and/or the like. Messaging may include control and display of text messages sent among one or more of the participants. Transfer control may include controls for transferring one or more participants to another patient care session or other video conferencing session, creating and managing sub-meetings involving a subset of the participants of the patient care session, and/or the like. Similarly, meeting control may include initiating the patient care session, ending the patient care session for a portion or all of the participants, presentation controls, and/or the like. Accessibility control may be used to customize the virtual care interface 102 to increase access, including, but not limited to, language accessibility, accessibility for hearing impaired, accessibility for visually impaired, and/or the like. For example, the virtual care system 202 may provide language interpretation services between participants in a patient care session in real time. The virtual care system 202 may utilize machine learning or other artificial intelligence to automatically detect an input language for the patient 104 and automatically translate the input language into a target language designated by the virtual care coordinator, a provider, and/or other user for presentation. Similarly, the virtual care system 202 automatically translates any input by other users in the patient care session into the input language for presentation to the patient 104. Accordingly, users conduct patient care sessions in real time, independent of language capabilities. The virtual care system 202 may similarly provide other accessibility services enabling patient care delivery for all patients, regardless of circumstance.

In one implementation, for safety and privacy, the virtual care interface 102 prevents the patient device 106 from directly initiating a patient care session, for example, by hosting the patient care session using the video conferencing application. Instead, as described above, the patent 104 may be automatically joined in the patient care session following initiation by the virtual coordinator system 208 and/or a provider session. The virtual care system 202 may automatically initiate patient care sessions based on a schedule or manually based on requests or patient needs. The patient 104 may request a patient care session using the virtual care interface 102, which will be coordinated by the virtual care system. The virtual care interface 102 may provide a notification, request permission, and/or take other precautions to ensure patient privacy prior to initiating a patient care session for the patient 104. For example, the virtual care interface 102 may present a request to the patient 104 asking permission to initiate a patient care session and capture a response from the patient 104. The request and the response may be captured using one or more input and output devices associated with the patient device 106. The request and/or the response may be audio, visual, and/or tactile. For example, the patient device 106 may present the request as an audio question or a visual question displayed with a display of the patient device 106. The response by the patient 104 may be a vocal response; a visual response, such as selection of yes, no, or reschedule options using a touchscreen or display of the patient device 106; a gesture response, and/or the like.

The patient 104 may receive care from a multi-disciplinary provider team independent of the location, with healthcare quality no longer limited by resources and providers available locally. The virtual care coordinator and/or the virtual coordinator system 208 may schedule patient care sessions for the patient 104 using the virtual care interface 102. For example, a primary care provider in Kansas may be providing coordinated care to the patient 104 in association with one or more specialists, such as a neurologist located in Florida. The virtual coordinator system 208 may initiate a first patient care session with the provider in Kansas and transfer the patent device 108 to a second patient care session with the specialist in Florida according to a schedule or a prompt by the provider or the specialist. The transfer may be initiated based on a prompt by the provider in Kansas or the specialist in Florida or otherwise by the virtual care coordinator. For example, the provider in Kansas may select an option to transfer the patient care session to the specialist in Florida, automatically transferring and joining the second patient care session and generating a communication to the virtual coordinator system 208 regarding the transfer.

Once the patient device 106 joins the second patient care session automatically, as described herein, the virtual care interface 102 accepts and manages input from the provider system 210 associated with the specialist in Florida. For example, the virtual care interface 102 may transfer control of the video conferencing application for the patient care session to the provider system 210 of the specialist in Florida, while the virtual care interface 102 monitors an activity of the patient care session. Stated differently, the content, information, and nature of the patient care session is not monitored for patient privacy and confidentiality. Instead, the activity monitored corresponds to whether the patient care session is active, inactive, or terminated. When the virtual care interface 102 detects that the patient care session is inactive or terminated, the virtual care interface 102 ends the visit mode and maintains the virtual care interface 102 in the locked state. Following termination of the patient care session, a communication may be sent to the virtual coordinator system 208 regarding the transition from the visit mode. In one implementation, the virtual care system 202 monitors connection between the various systems 206-210 and the video conferencing application. For example, the virtual care system 202 may detect whether a patient care session is running via the video conferencing application at predetermined intervals. If no patient care session is active, the virtual care system 202 ends the visit mode. When the virtual care interface 102 is not in visit mode for the patient device, the virtual care interface 102 awaits commands from the virtual coordinator system 208.

Such commands may correspond to the patient care sessions, patient messaging, patient observation and monitoring, patient resources, patient examination, and/or the like. In one implementation, the patient messaging captures and presents messages exchanged between the patient device 106, the virtual coordinator system 208, the provider systems 210, and/or other user devices. The messages may be presented using audio, visual, or tactile output. For example, the messages may be presented visually as text on a display of the patient device 106 or as audio using a speaker of the patient device 106. The patient 104 may utilize the patient messaging to exchange messages with the virtual care coordinator, members of the interprofessional care team, family or friends, or other designated users. The patient 104 may further utilize the patient messaging to send an invitation or prompt to visitors (e.g., family or friends) for a social visit. The invitation or prompt may be sent via short message service (SMS), text message, email, and/or other messaging service with a link or other access information for a patient care session. The virtual care interface 102 may be accessed using the user device to conduct the patient care session with one or more users at disparate locations, thereby facilitating a virtual visit and message exchange between the patient 104 and other users, such as visitors or care providers.

The virtual care system 202 may manage the messages to restrict the recipients, ensuring that only authorized and intended recipients receive the messages. For example, the patient systems 206 may correspond to a plurality of patients. In a hospital setting, each hospital room of a hospital may be associated with one of the patient systems 206, such that dozens of devices are connected to the virtual care system 202. This number may reach thousands when the hospital is part of a hospital care system including a plurality of hospitals at different locations.

The virtual care system 202 ensures that a message sent from or intended for one of the patient systems 206 is not sent to all the patient systems 206. Each of the patient systems 206 may be associated with a unique patient identifier that may be used to join the patient care sessions, as described herein. The unique patient identifier may be renamed as a patient room number or other name or location. Similarly, other devices, such as the provider systems 210 and the virtual coordinator system 208 may include unique identifiers. The unique identifiers may be used to direct patient messages to intended recipients.

The virtual care system 202 may control and coordinate the patient observation and monitoring. In one implementation, the virtual care system 202 provides virtual patient observation (VPO) using the patient system 206. The patient system 206 may capture real-time video of the patient 104, and the virtual coordinator system 208 monitors the real-time video of the patient 104. For example, where the patient 104 has a fall risk, a memory and/or functional impairment (e.g., dementia), or other condition posing a risk to the patient 104, the virtual coordinator system 208 monitors the patient 104 to identify and respond to any incidents involving the patient 104. In some cases, monitoring the patient may involve using artificial intelligence (AI) to identify a specific patient action or condition. For example, a machine learning model may be trained and used to identify when a patient has fallen or is experiencing discomfort, allowing an appropriate response to be taken.

The response may include dispatching a provider, such as a nurse, to the patient 104, providing audio, visual, and/or tactile feedback to the patient 104. In one example, the audio or visual feedback may include a message presented to the patient audibly or visually to inform the patient 104 that a provider is on the way or to prompt an action by the patient 104 (e.g., sit down, etc.). In another example, the tactile feedback may include vibration or similar tactile feedback to prompt an action by the patient 104. In one implementation, the virtual care system 202 facilitates live communication between the patient 104 and a virtual care coordinator, as described herein.

The patient resources may include online resources and other care resources, such as educational videos and content related to a condition of the patient 104, wellness, or other aspects of healthcare delivery or ancillary services. The patient resources may be saved and accessible locally on the patient device 106, via a cloud computing service, or otherwise via the network 204. The patient resources may include videos, audio, written content, interactive content, and/or other media. In one implementation, the virtual care interface 102 includes an integrated web browser that is displayed using the patient device 106 in a resource access mode.

The resource access mode presents patient resources identified using the virtual coordinator system 208 that are selected for, requested by, or otherwise customized for the patient 104, while preventing access to resources beyond the patient resources. For example, the virtual care coordinator may identify relevant videos for the patient 104 to watch at a scheduled time or otherwise as desired by the patient 104. The videos may be streamed or accessed locally. The virtual care interface 102 receives an identification of the relevant videos from the virtual coordinator system 208 and obtains, commands, or otherwise directs the relevant videos to play from the corresponding source. The patient resources may
include an online resource or webpage presented in the
resource access mode. The resource access mode may
prevent navigation away from the online resource or
webpage identified for the patient 104. In one example, the
webpage is presented without a navigation bar (e.g., URL
bar, address bar, etc.) and without or with limited navigation
buttons (e.g., forward, back, navigation tabs, etc.) in the
resource access mode. The virtual care interface 102 pro-
vides resources helpful and customized for the patient 104,
while ensuring the patient 104 does not access outside
resources that may introduce vulnerability to the virtual care
system 202 or otherwise are irrelevant to care of the patient
104. The virtual care interface 102 receives various com-
mands from the virtual coordinator system 202 to locate,
prepare, and present various patient resources in the resource
access mode.

The virtual care interface 102 may receive and execute
various commands related to patient examination using the
patient device 106 and the peripheral devices 108. The
peripheral devices 108 may include various medical devices
configured to capture patient medical data for the patient
104, including, without limitation, a stethoscope, an oto-
scope, an ultrasound device, thermometer, electrocardio-
gram, pulse oximeter, blood pressure gauge, dermatology
scope, and/or other sensors, instruments, and devices. The
virtual care interface 102 may obtain the patient medical
data automatically or manually from the peripheral devices
108. In some scenarios, the patient medical data is presented
to a provider using the provider system 210 and/or the
virtual care coordinator using the virtual coordinator system
208 during or outside of a patient care session. In one
implementation, the patient medical data is captured during
the patient care session and presented in real-time to the
provider and/or virtual care coordinator. Where the patient
medical data includes audio or visual data, the virtual care
interface 102 selectively transitions between the patient
device 106 and the peripheral device 108 for presentation in
real time.

In some aspects, the patient medical data may include
electronic medical records (EMR) integrated with the virtual
care system 202. For example, EMR such as patient regis-
tration, labs, imaging, micro, vitals, orders, or documenta-
tion reviews may be stored for later retrieval. The virtual
care system may also facilitate placing orders (and order
sets) of lab results via the virtual care system 202. The
virtual care system 202 may obtain and normalize incoming
EMR and similar data having different formats into a single
standardized format and send out the data in the standard-
ized format to one or more destinations, such as other
medical facilities or systems. Accordingly, the virtual care
system 202 generates source independent standardized
EMR.

In one implementation, the virtual care interface 102 is
configured to receive coordinator commands from the vir-
tual coordinator system 208 and generate session commands
from the coordinator commands to transition between audio
inputs and video inputs. More particularly, the patient care
sessions may be executed using a video conferencing appli-
cation, as described herein, with the video conferencing
application configured to execute session commands spe-
cific to the video conferencing application. The virtual care
interface 102 translates coordinator commands received
from the virtual coordinator system 208 into the session
commands for performing specific functions using the video
conferencing application. Stated differently, the virtual care
interface 102 converts the coordinator commands into a format mimicking the session commands of the video con-
ferencing application. Further, as described herein, the
access restriction system intercepts input when in the visit
mode. Thus, in one implementation, the virtual care inter-
face 102 temporarily transitions the visit mode into a periph-
eral input mode to accept input in the form of the session
commands, while continuing to intercept other input as
described herein. The peripheral input mode may present the
virtual care interface 102 as semitransparent in this manner.
Once the session commands are input to the video confer-
encing application, the virtual care interface 102 is transi-
tioned back into the visit mode. The virtual care system 202
controls the audio input and video input during the patient
care session in this manner.

In one implementation, the virtual care interface 102 is
configured for translating the coordinator commands into the
session commands by transitioning the virtual care interface
102 into the unlocked state and correlating screen coordi-
nates corresponding to the session commands with the
coordinator commands. For example, the video conferenc-
ing application executing the patient care sessions may
include visual options, such as in the form of drop-down
menus, for selection using a cursor. In the unlocked state, the
virtual care interface 102 may present a cursor coordinate
marker correlated to a particular coordinator command,
which a technician may move to the screen coordinates
associated with the corresponding visual option. Accord-
ingly, when the virtual coordinator system 208 issues the
particular coordinator command, the virtual care interface
102 will automatically temporarily transition into the periph-
eral input mode, provide input to the video conferencing
application in the form of a corresponding session command
by moving the cursor to the screen coordinates and clicking
the cursor, and transitioning the virtual care interface 102
back into the visit mode. Such configuration and commands
may be used for a plurality of audio inputs, video inputs,
and/or the like.

The virtual care interface 102 may configure the video
conferencing for conducting the patient care sessions with a
set of primary inputs and a set of peripheral inputs. The set
of primary inputs may include a primary audio input for
capturing vocal input from the patient 104 and any other
personnel present with the patient 104, and a primary visual
input for capturing images or video of the patient 104 and
any other personnel present with the patient 104. For
example, the primary audio input may be a microphone of
the patient device 106, and the primary visual input may be
a camera of the patient device 106. The set of peripheral
inputs may include the audio input and visual input of one
or more of the peripheral devices 108 associated with the
inputs configured for the coordinator commands. For
example, the video conferencing application may include a
set of audio input options, including microphone one and
microphone two, and a set of visual input options, including
video one and video two. The set of primary inputs may
include microphone one and video one, and the set of
peripheral inputs may include microphone two and video
two. Taking a digital stethoscope and a digital otoscope as
examples of the peripheral devices 108, microphone two
may correspond to an audio input associated with the digital
stethoscope, and video one may correspond to a video input
associated with the digital otoscope. During a patient care
session, the virtual coordinator system 208 may issue com-
mands, which may be prompted by a provider or other
personnel, to switch between microphone one and micro-
phone two or between video one and video two, and the
selected input is presented during the patient care session.

For example, during a patient care session between the patient 104 and a provider, the audio input may be switched from microphone one to microphone two, where the audio presented during the patient care session changes from the voice of the patient 104 to the heartbeat of the patient. The peripheral devices 108 may be further controlled using commands executed via the virtual care interface 102 to pan, tilt, zoom, change orientation, change location, and/or the like. Such commands may be carried out manually (e.g., with assistance from an on-site nurse) or automatically using robotics or functionality of the peripheral devices 108. Accordingly, the provider may conduct a patient examination of the patient 104 during a patient care session using the peripheral devices 108 independent of location.

The virtual care system 202 provides robust patient care for patients that are in remote locations, quarantined, or disposed in other environments by combining multiple modalities of care into a single digital healthcare platform. In one implementation, patients are placed into patient care hubs based on location, diagnosis, needs, and/or the like. The patient care hubs may be used to connect patients with relevant providers, support groups, and other resources. As an example, the patient 104 may live in an area of rural South Dakota where there are no neurologists and suffer a stroke. The patient 104 is admitted to a hospital and the virtual coordinator system 208 identifies a neurologist with the relevant expertise in Massachusetts and facilitates a patient care session with the neurologist. At the hospital in South Dakota, the providers deliver care to the patient pursuant to the expertise of the neurologist. The neurologist may continue to round the patient 104 using patient care sessions to monitor recovery progress, without being present. The virtual coordinator system 208 may identify a speech therapist to further facilitate recovery for the patient 104 via patient care sessions. Patient care sessions may be conducted between various providers of an interprofessional medical team for the patient 104. For example, the primary care provider may coordinate care delivery with the neurologist or other personnel. Further, if the patient 104 has questions or is not feeling well, the call light may be used to access the virtual coordinator system 208 to direct the patient 104 to the relevant resource or personnel regardless of location. Even after discharge, the recovery and condition of the patient 104 may continue to be monitored without interruption. The virtual care system 202 ensures that the people, rather than the location, take care of the patient 104. In other words, the patient 104 has access to the same level of care in rural South Dakota as someone in Boston. The patient care hubs may further be used in providing care to the patient. For example, the patient 104 may be placed in a stroke care hub, a South Dakota care hub, and/or the like to further customize care and resources for the patient 104 according to patient needs.

Care may similarly be expedited. When care is location based, there is often a long wait time to meet with a specialist. The virtual coordinator system 208 identifies relevant specialists and selects a specialist based on availability and/or priority. For example, the virtual coordinator system 208 may identify a set of one or more specialists having an expertise for a condition of the patient 104. The virtual coordinator system 208 may select one of the specialists according to which of the set of specialists is available the soonest. The virtual coordinator system 208 may further schedule or select the specialists according to a priority assigned to the condition of the patient 104. For example, if the condition of the patient 104 involves an urgency and a first availability of a specific specialist is too far out, the virtual coordinator system 208 may adjust the schedule of the specific specialist to elevate a patient care session for the patient 104 according to the priority.

The virtual care system 208 is directed by a virtual care coordinator who may be human, an artificial intelligence, or a combination of both. The virtual care coordinator may be a nurse practitioner who oversees patient care for a plurality of patients and facilitates patient care sessions with and among providers associated with the patient care using the patient systems 206 and the provider systems 210. The virtual care coordinator may alternatively or additionally correspond to one or more automated systems to identify and coordinator providers, ancillary services, and other aspects of patient care. The virtual care coordinator may include an artificial intelligence that receives input, such as patient input from the patient 104 and patient medical data for the patient 104, and generates a care plan and coordinates involvement with the relevant providers. For example, the virtual care coordinator of the virtual coordinator system 208 may automatically facilitate virtual medicine, behavioral health, mental wellness checks, and more and determined when to involve a provider or other professional. Various users may be involved using the patient systems 206, the provider systems 210, and/or other user devices over the network 204.

In some implementations, the virtual care system 208 may receive notes from the provider with regards to one or more patients. For example, patients may be monitored by different providers during different shifts. Thus, each provider may enter specific notes into the system to other providers with regards to one or more patients to facilitate a handoff from one provider to another.

In one implementation, the network 204 includes one or more networks (e.g., the Internet, an intranet, a Virtual Private Network (VPN), a Voice over Internet Protocol (VoIP) network, a wireless network, a cellular network, satellite, etc.) providing access to and interaction with the virtual care system 102. A user, such as a patient, provider, or other personnel, accesses and interacts with the virtual care interface 102 using a user device to access or provide care delivery via the network 204.

The user device is generally any form of computing device capable of interacting with the network 204, such as a controller, a personal computer, terminal, workstation, portable computer, mobile device, tablet, phone, pager, multimedia console, or other Internet Protocol (IP)-based telecommunication devices, which may or may not form or be part of the systems 206-210. The network 204 is used by one or more computing or data storage devices (e.g., one or more databases 212 or other computing units described herein) for implementing the virtual care interface 102 and other services, applications, or modules in the network environment 200.

In one implementation, the network environment 200 includes at least one server 214 hosting a website or an application that the user may visit to access the virtual care interface 102 and/or other network components or related services. The server 214 may be a single server, a plurality of servers with each such server being a physical server or a virtual machine, or a collection of both physical servers and virtual machines. In another implementation, a cloud hosts one or more components of the network environment 200. The server 214 may represent an instance among large instances of application server in a cloud computing environment, a data center, or other computing environment. The user devices, the systems 206-210, the server 214, and other resources connected to the network 204 may access one or more other servers to access to one or more websites, applications, web services interfaces, storage devices, computing devices, or the like that are used for virtual healthcare delivery. The server 214 may also host a search engine that the virtual care interface 102 uses for accessing, searching for, and modifying patient data, provider data, education data, and other data. The virtual care interface 102 may utilize a cloud messaging service to facilitate real time communication. Users may access and interact with the virtual care interface 102 with software running on the user device utilizing an interface such as an application programming interface (API). Stated differently, the API can be called from an application or other software on the user device to pull or push data to and from the virtual care system 202 over the network 204.

Figure 3:
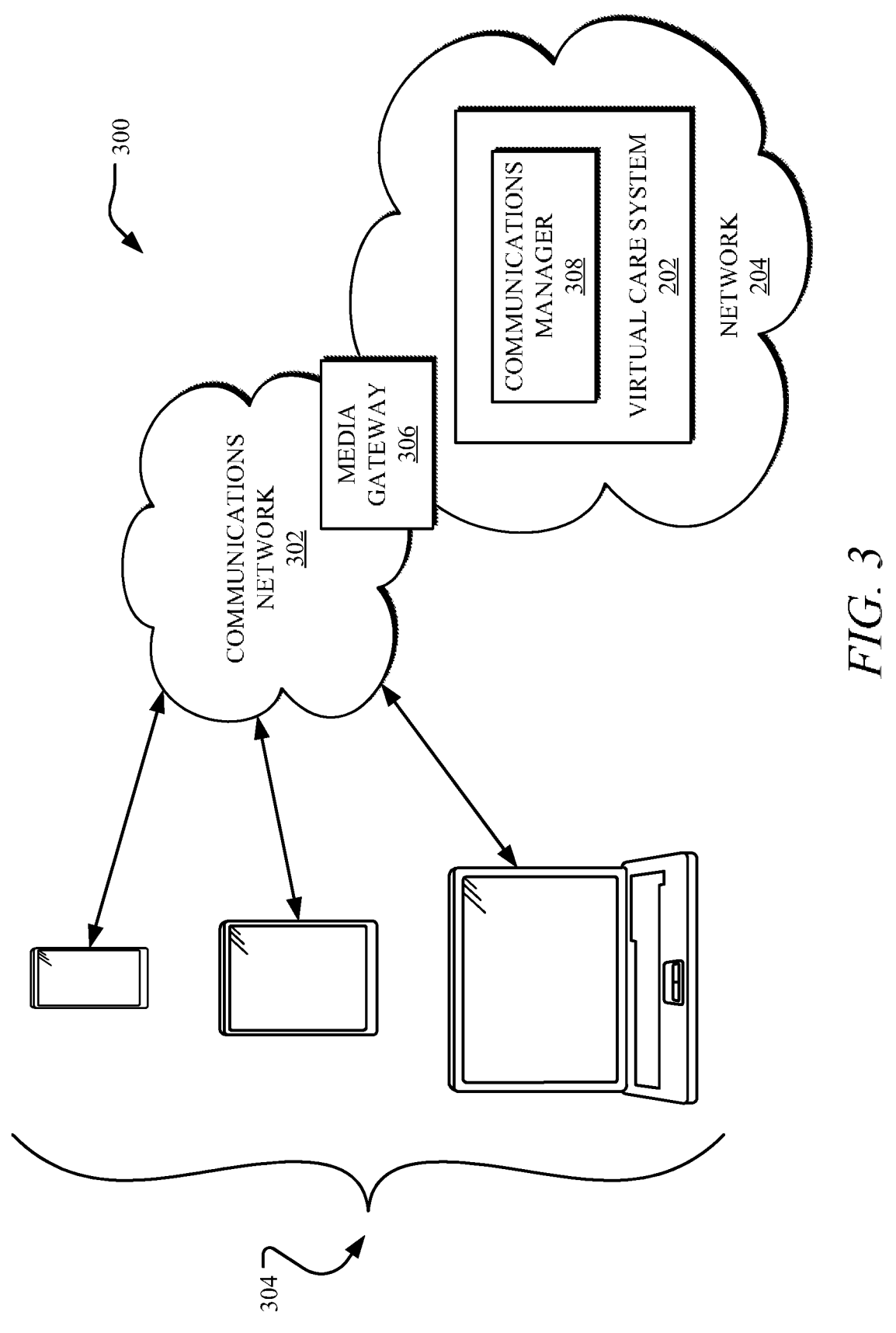
FIG. 3 depicts an example network environment for communicating over one or more communications networks in connection with virtual patient care.

Turning to FIG. 3, an example network environment 300 includes the virtual care system 202 accessible via one or more communications networks in connection with virtual patient care. In one implementation, the network environment 300 includes one or more Voice over Internet Protocol (VoIP) communication sessions set up between users in connection with the patient care sessions using an Internet Protocol (IP) based communication protocol, such as Session Initiation Protocol (SIP) in association with the video conferencing application of the virtual care interface 302. The network 204 hosting the virtual care system 202 may be accessible with one or more communications networks 302, which may implement a VoIP environment. However, portions of the communications network(s) 302 may include non-Internet Protocol (IP)-based routing. It will be appreciated that the presently disclosed technology may be applicable to any configuration of communications network(s) 302 and/or any communications network environment. The communications network(s) 302 may include numerous components such as, but not limited to gateways routers, servers and registrars, which enable communication across the communications network(s) 302.

In one implementation, the communications network(s) 302 includes multiple ingress/egress routers, which may have one or more ports, in communication with the network 204. The edge devices are network devices that provide entry points into the network 204 via the communications network(s) 302. Stated differently, one or more users may connect to the virtual care system 202 with a user device 304 using one of the edge devices via components of the communications network(s) 302. One or more customer home or business local area networks (LANs), where a user will connect with the network 204 via the communications network(s) 304 with the user device 304 connected to a router. In another example, the user devices 304 access, and are accessed by, the network 204 via the communications network 304, which may be a public switched telephone network (PSTN) operated by a local exchange carrier (LEC). The communications network(s) 304 may communicate with the network 204 through a media gateway device 306. Communication via any of the networks can be wired, wireless, or any combination thereof. The user device 304 may be any form of computing device, as described herein, including, without limitation, a personal computer, a terminal, a workstation, a mobile phone, a mobile device, a tablet, a multimedia console, a television, an Internet of Things (IOT) device, and/or the like. The user devices 304 may be integrated with, be part of, form, or otherwise be associated with the systems 206-210 and the corresponding input and output devices.

In one implementation, the user devices 304 use the virtual care system 202 for real-time interactive patient care sessions using the video conferencing application. A communications manager 308 may control or otherwise facilitate the video conferencing application of the virtual care system 202. The server 214 may host the patient care sessions and transmit and receive video, image, and audio data to and from each of the user devices 304. In one implementation, each of the user devices 304 hosts an application facilitating communication between the user devices 304 and the server 214. The server 214 may maintain a list of the identifiers, including patient and provider identifiers, each associated with one of the user devices 304 and/or one of the users. Within the network environment 300, the virtual care system 202 may facilitate patient care sessions independent of the type of user device utilized.

Figure 4:
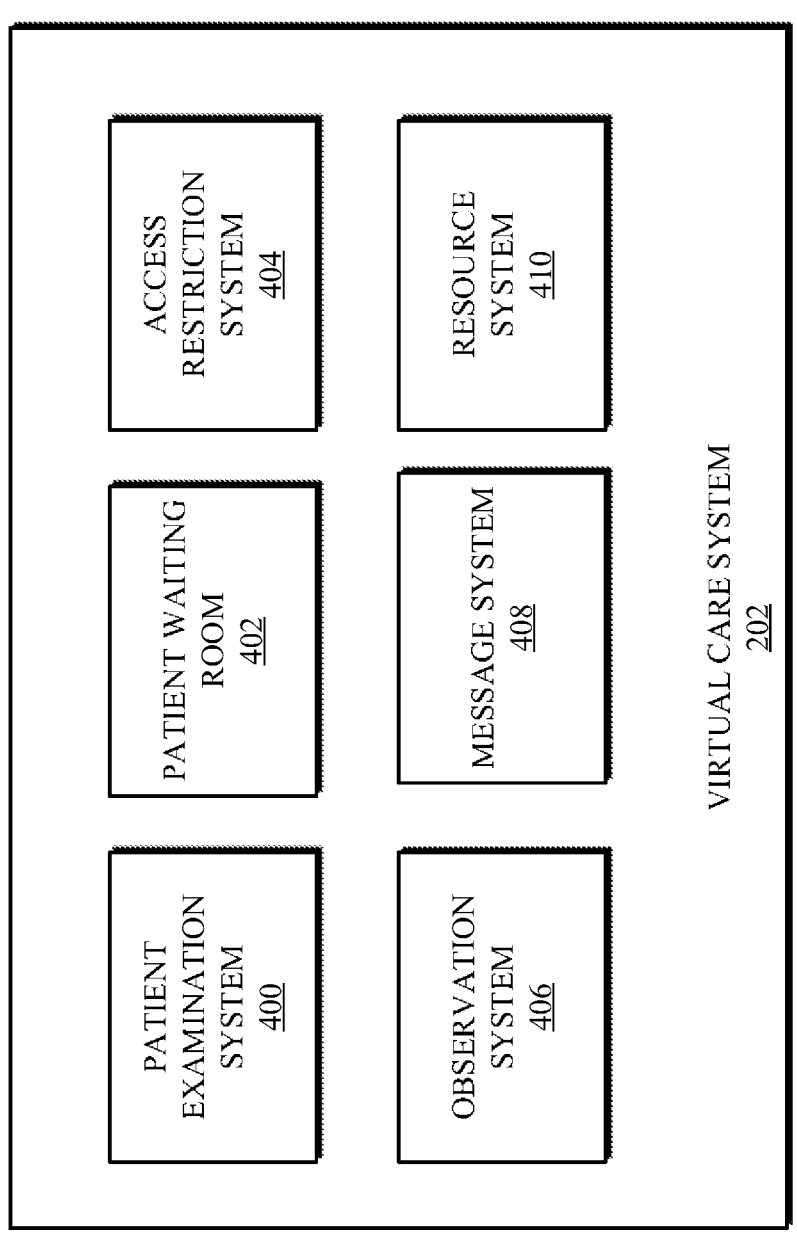
FIG. 4 shows a block diagram of an example virtual care system for providing virtual care.

Referring to FIG. 4, a block diagram of the virtual care system 202 illustrating various systems for providing virtual care is shown. In one implementation, the virtual care system 202 includes, without limitation, a patient examination system 400, a patient waiting room 402, an access restriction system 404, an observation system 406, a message system 408, and a resource system 410. The patient examination system 400 may control various aspects of the patient care sessions, including video conferencing, control of the peripheral devices 108, and/or the like, and the access restriction system 404 may control the various states and modes of the virtual care interface 102 to control access, interaction, presentation, and input, as described herein. The resource system 410 may control the access to, interaction with, and presentation of care resources, as described herein.

The patient waiting room 402 may maintain patients and other users in a queue for specific users, including providers, patients, and the virtual care coordinator. For example, the video conferencing application of the virtual care system 202 may maintain patients in a waiting room until the patient care session can begin. The patient waiting room 402 may further manage call lights from the patient systems 206. In one implementation, the communications manager device 212 utilizes SIP to route communications (e.g., video, audio, multimedia, text, or other content communications) within the network environment 300 to the appropriate party, such as providers (e.g., to the provider systems 210), the virtual care coordinator (e.g., to the virtual coordinator system 208), and the patients (e.g., the patient systems 206). The communications manager 308 integrates inbound and outbound voice applications with Internet applications to provide various communication services, including real-time conferencing, collaborating, and messaging, while supporting multiple interactions simultaneously independent of the communications channel. The communications manager 308 may route requests for patient care sessions among the user devices 304, as appropriate.

The patient waiting room 402 may be configured to maintain a call queue of communications for acceptance by specific user devices 304. The patient waiting room 402 may maintain the communications according to an assigned priority. For example, in initiating the communication, the patient 102 or a provider may indicate whether there is an elevated priority. The patient waiting room 402 may further distinguish patient initiated communications from provider initiated communications within the call queue, for example, based on an identification of the device from which the communication originated (e.g., using the IP address of the device) or through input captured using the user device 304. Management of patient call light responses within the patient waiting room 402 ensures the correct provider or other person joins a patient care session in a timely manner. In one implementation, the patient waiting room 402 receives a call from the patient system 206 and places the call in a queue. The call may be placed in the queue according to a priority or urgency of the call. The virtual provider system 204 then analyzes the nature of the call and matches the call to the appropriate user(s), who are then notified using the communications manager 308 and dispatched for response.

In one implementation, the call light of the patient waiting room 402 is presented using the virtual coordinator system 208 as a highlighted section. The call light section may include a list of rooms (e.g., using a patient identifier, room number, etc.) with each room in which the call light was triggered highlighted. The rooms may be highlighted using color, flashing light, graphics, and/or other distinguishing visual features. The highlighted rooms may be selected to turn the call light on or off as appropriate. Further, the highlighted room may be selected to initiate a patient care session. In one particular example, the virtual coordinator system 208 includes a first screen displaying the call light section and a second screen displaying the patient care sessions and virtual patient observation.

The patient examination system 400 may utilize the peripheral devices 108 including wearables worn by the patients to capture patient medical data, such as patient vitals, at regular intervals. The patient examination system 400 may analyze the patient medical data against thresholds based on patient profiles, and/or standards. When the patient medical data is outside the thresholds, the virtual care system 202 may automatically connect the patient system 206 to the patient waiting room 402 for a patient care session, automatically add the patient 104 to a triage list for a provider to visit along with relevant information explaining the nature of the issue, automatically initiate hospital admission for the patient 104. In one example, the patient examination system 400 may be monitoring the patient 104 at home using a wearable including a pulse oximeter. Upon detection of decreasing oxygen levels, the virtual care system 202 may automatically send an alert to the patient 104 to go to the emergency room and coordinate the admission of the patient 104 with the emergency room.

The observation system 406 providers VPO of a plurality of patients. The observation system 406 may be used to monitor patients (e.g., using a machine learning model) that are high risk (e.g., fall risk), being treated for a highly communicable but deadly disease where constant monitoring is needed but access is limited, and/or the like. In one implementation, the observation system 406 facilitates observation, while ensuring patient privacy. For example, the observation system 406 may capture real time video of the plurality of patients and present the video to a virtual care coordinator using the virtual coordination system 208. However, in presenting the videos associated with the plurality of patients simultaneously, the observation system 406 prevents the plurality of patients from seeing or hearing each other. More particularly, the observation system 406 commands the patient systems 206 to mute the audio input and output and the virtual care interface 102 is in the locked state in an observation mode where the video conferencing application is not visible, thereby blocking any display of video. In the observation mode, the virtual care interface 102 is opaque. The virtual coordination system 208 may selectively unmute the audio input or output of a specific patent system 206, for example to interact with the patient or hear what is occurring with the patient.

To ensure that the audio input or output of one or more of the patient devices 206 is not inadvertently left unmuted, in one implementation, the observation system 406 automatically issues a command to all the patient systems 206 associated with the plurality of patients at regular intervals (e.g., ten seconds) to mute the audio input and output. Additionally, the observation system 406 may generate a notification presented via the patient system 206 and the virtual coordinator system 208, providing a visual cue to the virtual care coordinator and anyone present with the patient that the patient is being monitored.

The observation system 406 may operate in conjunction with the access restriction system 404 to permit and initiate video capture using the patient device 106. As described herein, the virtual care interface 102 translates coordinator commands received from the virtual coordinator system 208 into the session commands for performing specific functions using the video conferencing application, such as initiating video. At regular intervals (e.g., ten seconds), the observation system 404 issues coordinator commands to detect a presence of a start video option and if so, select the option to start video capture. These coordinator commands are converted into corresponding session commands and executed with the patient system 206. Accordingly, the observation system 406 and the access restriction system 404 facilitate continuous real time monitoring of the plurality of patients.

The message system 408 controls and coordinates messages exchanged among the various user devices 304, including the systems 206-210. In one implementation, a message intended for a particular recipient is directed to the particular recipient using the message system 408 associated with the communication manager 308. Each message may include an identifier associated with a recipient (e.g., the patient identifier, the provider identifier, etc.), a message identification designating the information as a message, and the content of the message. The message system 408 parses the message to identify the identifier, the message identification, and the message content. Upon identifying that the information contains a message using the message identification, the message system 408 routes the message to the user device 308 of the recipient using the identifier, and the user device 308 presents to the message content. In one implementation, the virtual care interface 102 may transition into a message mode to present the message with the virtual care interface 102 in a semitransparent state. The messages may be customized, sent at regular intervals (e.g., get well messages, information about particular services, etc.), and/ or in response to particular scenarios, detected conditions, or triggers.

Figure 5:
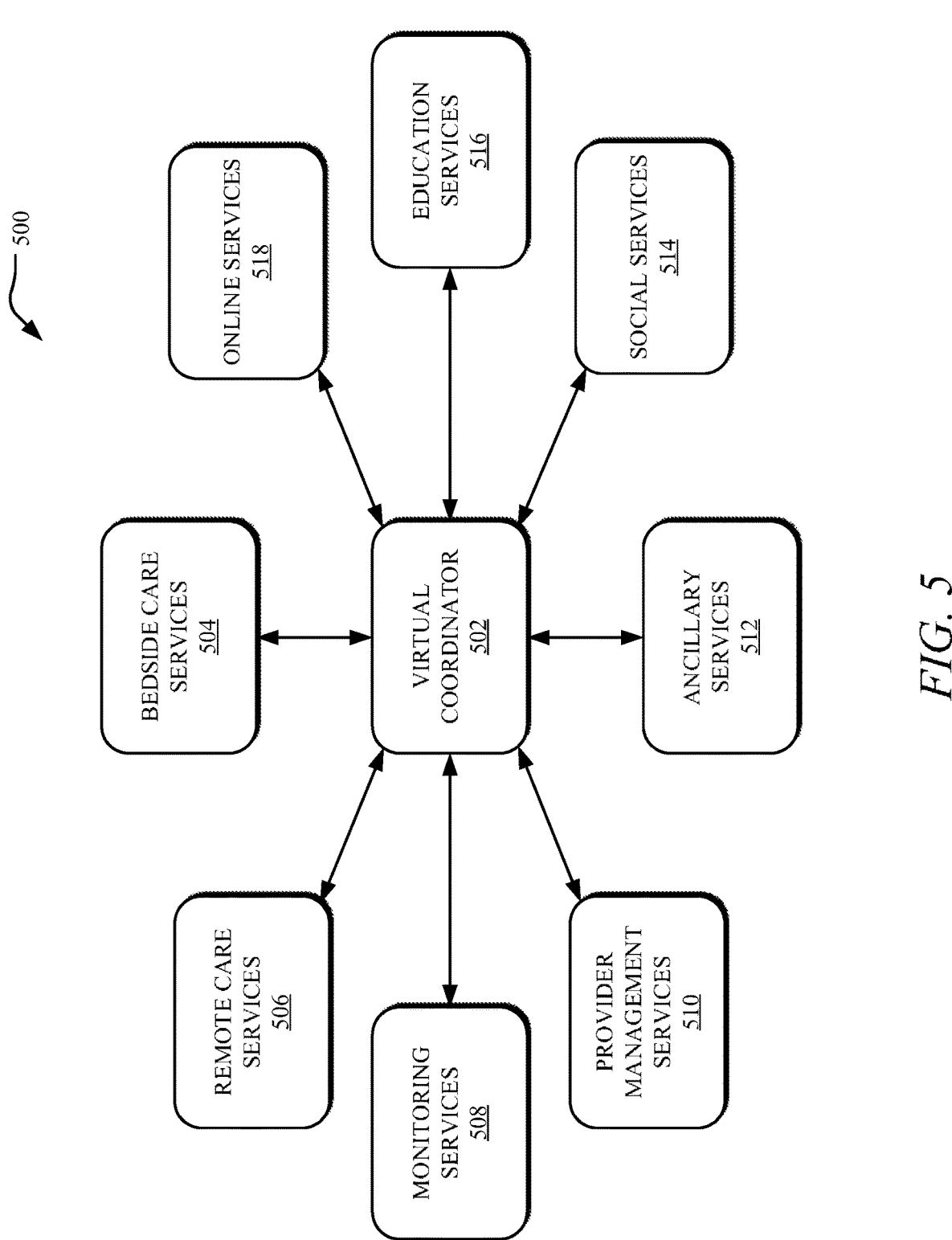
FIG. 5 shows example services executed by a virtual care coordination system of the virtual care system.

It will be appreciated that various services may be controlled, provided, or executed by the virtual coordinator system 208 of the virtual care system 202. Turning to FIG. 5, example virtual services 500 facilitated by a virtual care coordinator 502 associated with the virtual coordinator system 208 are shown. As described herein, the virtual care coordinator 502 may be a human provider, an artificial intelligence, a collection of autonomous services, or a combination of these aspects. In one implementation, the virtual services 500 include, without limitation, bedside care services 504, remote care services 506, monitoring services 508, provider management services 510, ancillary services 512, social services 514, education services 516, and online services 520.

The bedside care services 504 involve the virtual care coordinator 502 checking on patients or conducting rounds without the patients needing to directly interact with the patient system 206. In one implementation, the virtual care coordinator 502 may activate the patient device 106, which automatically joins a patient care session with the virtual care coordinator 502 via the virtual care interface 102. Similarly, a patient care session may be initiated from the patient side. The call light of the virtual care interface 102 may be used to initiate a patient care session with the virtual care coordinator 502. The virtual care interface 102 may detect a presence of a provider, such as a nurse, with the patient 104 and automatically initiate a patient care session with the virtual care coordinator 502. For example, the virtual care interface 102 may detect the presence of the provider using facial recognition, object recognition, using gesture commands, based on a presence of an electronic device associated with the provider, or using other authenticated commands. The virtual care coordinator 502 may supplement the care provided by the bedside nurse in a multidisciplinary rounding and/or provide remote training or mentorship for the bedside nurse. Following the initiation of the patient care session, a request or notification is sent to the virtual care coordinator 502 for the patient care session. The virtual care coordinator 502 may then join the patient care session or send a message in response for presentation with the patient device 106.

The remote care services 506 permit a provider or other approved user at a remote location to join a patient care session with the patient 104, as coordinated by the virtual care coordinator 502. The virtual care interface 102 may include an active caregiver directory login. The active directory login may prompt providers to login before accessing a provider interface. Various levels of user access may be provided with different login credentials (e.g., logins for admins, virtual provider, virtual nurse, virtual coordinator, etc.). Each of the different levels of user access may provide different levels of control of patient care sessions. In some cases, social visits may be facilitated using the virtual care system. For example, user accounts may be opened for a patient's relatives. By logging into an account, the patient's relatives can see and talk to the patient during scheduled social visiting hours.

In one implementation, the provider interface may display a directory of units, virtual services, active patients, and/or other options and resources. In one implementation, the virtual care interface 102 presents the provider interface with options in the form of a list of units or virtual services. Upon selection of one of the options, the virtual care interface 102 automatically joins a patient care session between the provider and the virtual care coordinator 502. The virtual care coordinator 502 provides an update on the patient 104 to the provider, and the virtual care interface 102 automatically joins the patient device 106 in the patient care session. The provider can conduct patient care sessions with any relevant personnel regarding patient care for the patient 104 in this manner, with or without the patient 104 or the virtual care coordinator 502 involved. A patient care session involving a social visit with a family member or friend of the patient 104 may similarly be conducted in this manner.

During patient care sessions in connection with the bedside care services 504 or the remote care services 506, the virtual care coordinator 502 or a provider may share the screen of the user device with the patient 104 using the virtual care interface 102. The screen sharing may be used to present provider notes, imaging, labs, telemetry, whiteboard education, and/or other patient medical information or care resources. The virtual care coordinator 502 may similarly provide messages for the patient 104, such as upcoming appointments, sentiments, advertisements, call light responses, and other information. The messages may be provides at regular intervals automatically or upon initiation by the virtual care coordinator 502. Additionally, the virtual care coordinator 502 or a provider may control the use of the peripheral devices 108, as described herein.

The monitoring services 508 involve virtual patient monitoring, as described herein. In one implementation, the virtual coordinator system 208 instructs each of the patient systems 206 for a plurality of patients involved in the virtual patient monitoring to coordinate the patient systems in a consolidated patient care session including the plurality of patients. In this manner, the virtual care interface 102 presents a consolidated interface including real time video of each of the plurality of patients. The virtual care coordinator 502 can see all of the plurality of patients and interact (e.g., via audio or video) with each of the plurality of patients independently, while ensuring that the plurality of patients cannot see or hear each other.

The provider management services 510 facilitate coordination of providers to create and manage an interprofessional team of providers for the patient 104 independent of location. The provider management services 510 identify relevant providers for each need of the patient 104 and select a provider from the relevant providers based on availability, priority, and other factors. The virtual care coordinator 502 facilitates patient care sessions with the provider, the patient 104, and/or other personnel and members of the interprofessional team, as appropriate. The provider management services 510 may further manage patient waiting rooms corresponding to each of the providers. Similarly, the provider management services 510 may be used to manage resources available to the providers in connection with care delivery.

The ancillary services 512 provide access to ancillary services, such as a pharmacy, other units, physical therapy, speech therapy, wellness, mental health, smoking cessation, specialists, and other services related to the care of the patient 104. Similarly, the social services 514 provides access for the patient 104 to social services, such as support, counseling, programs, subsidies, childcare, and/or the like. In one implementation, the patient 104 may join or be involved in a patient care session with the virtual care coordinator 502 and have a need for the ancillary services 512 or the social services 514. The virtual care coordinator 502 may transfer the patient device 106 to the appropriate service 512, 514, where the patient device 106 automatically joins a patient care session with the service 512, 514 or is automatically placed in a patient waiting room for the service 512, 514. The patient 104 may leave a hospital with follow up services already scheduled.

The education services 516 and the online services 518 may provide various types of content and care resources for presentation to and/or interaction with the patient 104. For example, the virtual care coordinator 502 may instruct the virtual care interface 102 to play an educational video for the patient 104. The educational videos may be streamed or stored locally. Similarly, the virtual care coordinator 502 may instruct the virtual care interface 102 to open an integrated web browser for the patient 104. The integrated web browser may provide access to online scheduling, support groups, education modules, and/or other care resources. The virtual care coordinator 502 may remotely control the integrated web browser to guide the patient 104.

The virtual care coordinator 502 provides and facilitates the services 504-518, while ensuring privacy and security. The virtual care system 202 simultaneously protects the privacy of the patients and the security of the virtual care system 202 using the various features discussed herein. For example, the identifier presented in connection with the patient care sessions may be connected to the room of the patient or other unique but anonymized identifier, where no patient information is collected or shared. An alert, such as an audio or visual alert, may be used to notify the patient 104 and any others that a patient care session has been activated using the patient device 106. The camera of the patient device 106 may always default to off until permission is granted from the patient 104. The patient 104 is unable to access any functionality of the patient device 106 outside of designated controls using the access restriction system 404.

The virtual care system may be integrated with a staff secure messaging system to facilitate sending secure texts, voice messages, and two way communications directly to a caretaker like a nurse or a provider. In some implementations, the virtual care system may facilitate regular SMS and phone calls to a patient.

There are many advantages and improvements to patient care delivery using the virtual care system 202. For example, the virtual care system 202 contributes to quality care and protocol compliance in areas including, without limitation, fall monitoring, CLABSI/CAUTI/skin protocol compliance, capture of declining patient status, and patient education. The virtual care system 202 may further capture instances of potential missed care, such as unnecessary restraints (e.g., four side rails), missed regular rounds, missing nutrition, missing documentation, missing vitals/I&O, missing PICC line dressing changes, unapplied allergy bands, and/or the like. Additionally, the virtual care system 202 improves patient morale, particularly for quarantined patients, for example through virtual family and friends visits. The virtual care system 202 improved: efficiency (e.g., saved staff and provider time), documentation (e.g., ensuring accuracy and completion of documentation), patient satisfaction (e.g., assisting with family visit and care plan explanation), discharge (e.g., assisting with completion of discharge/ transfer orders and providing patient education), admissions (e.g., assisting with scribing admission assessment, completion of patient history, coordination and capture of medical history and medications), fall reduction (e.g., virtual patient monitoring and intervention), skin and wound treatment and CLABSI (e.g., monitoring of compliance with protocols and reminders to providers), CAUTI (e.g., assistance with discontinuation of unnecessary catheters), PPE reduction, stay length (e.g., assistance with care plan to advance discharge), throughput, sepsis alerts, provider communication, patient status (e.g., monitoring patient status for decline), provider mentoring and training, etc.

In some specific examples, the virtual care coordinator 502: observed a patient having a seizure and coordinated care, while a bedside nurse attended to the patient; assisted a new beside nurse address a malfunctioning chest tube; conducted rounds with a physician to understand the care plan for a patient and coordinated the care plan; and tracked a need for a procedure and coordinated with the hospitalist to schedule it outpatient. In one example, a patient may be admitted into the ER with a stroke and a neurologist may join a patient care session to provide expertise directly in connection with the team present in the ER. During hospitalization, the neurologist may conduct rounds on patients and facilitate physical therapy, occupational therapy, and speech therapy remotely. Case management may conduct a virtual tour of the facility, and patient and family may speak with virtual palliative care. The virtual care system 202 may be used in connection with discharge planning, including a virtual pharmacist assisting with medication and discharge instructions, educational videos and web modules, and a virtual health coach virtually visiting with the patient, family, or care givers to coordinate ambulatory care. At home, the virtual health coach may coordinate care and monitor the patient to prevent readmission, the neurologist may monitor progress closely without requiring the patient to travel for appointments or use certain software programs, a primary care provider and the neurologist may conduct patient care sessions with the patient jointly or separately, and therapy can continue at home.

Generally, the virtual care system 202 may be used in connection with tele-stroke, virtual transfer center, tele-ER, eICU, tele-pharmacy, virtual rounds, virtual monitoring, hospital at home, telehealth kiosk, critical access hospital support, and providing location independent care delivery, among other services and benefits. The tele-stroke may include sending a notification to a neurologist to join a patient care session with the virtual care coordinator 502, the neurologist joins the patient care session with the virtual care coordinator 502 to obtain information regarding a patient, and the virtual care coordinator 502 transfers the neurologist to the emergency room to join a patient care session with an in-person team treating the patient.

The virtual transfer center may include: the virtual care coordinator 502 notified of a transfer, the virtual care coordinator 502 contacting the transfer center, a new patient care session being created by the transfer center, providers at different facilities being notified to join the patient care session, the providers joining the patient care session, and the virtual care coordinator 502 activating the patient system 206 to join the patient waiting room or the patient care session. A virtual clinical hub may serve as a coordinator for a plurality of clinics. The virtual care coordinator 502 may monitor the call lights across clinics, where if a clinic pushes the call light, the virtual care coordinator 502 answers and identifies the services needed. The service joins a patient care session between the clinic and service or transfers the clinic to the patient care session of the service.

In one example of virtual rounding, the provider joins the virtual care coordinator 502, the provider requests a connection with a patient, and the virtual care coordinator 502 activates a patient care session with the provider and the patient. In an example of bedside rounding, the provider uses the call light to reach the virtual care coordinator 502, the virtual care coordinator 502 receives an alert associated with the call light, and the virtual care coordinator 502 joins a patient care session for the patient.

In connection with virtual ancillary services, the services may join the virtual care coordinator 502 and request a patient, and the virtual care coordinator 502 activates a patient care session for the patient and service. Using the patient waiting rooms 402, multiple patients and ancillary services may be simultaneously facilitated. The tele-pharmacy may include the virtual care coordinator 502 identifying a patient needing discharge medication education, the virtual care coordinator 502 transferring the patient to a patient care session with the discharge virtual pharmacist, placing the patient in the patient waiting room or joining the patient in the patient care session, and automatically removing the patient from the patient care session following the session.

The virtual monitoring may include the virtual care coordinator 502 activating patient observation mode using the virtual care interface 102, and automatically joining selected patient systems 206 to a patient care session in the form of a patient observation session, where the virtual care interface 102 is in the observation mode. All the patient systems 206 selected are admitted into the patient observation session and approval is obtained from each of the associated patients to initiated video monitoring. Individual patients may be viewed or interacted with separately, while monitoring all the rooms simultaneously. Similarly, an eICU may utilize the virtual monitoring to view all the rooms simultaneously and interact with the rooms one at a time. The virtual care coordinator 502 may also join bedside rounding to monitor patients.

The virtual care coordinator 502 may facilitate patient care sessions in the form of social visits with family and friends. The virtual care coordinator 502 may obtain consent from the patient and coordinate time with visitors. The visitors join the patient care session in a subroom. A virtual health coach may act as the virtual care coordinator 502, where patients can check-in using the call light, the virtual care coordinator 502 can send messages to the patients, provide care resources, transfer the patient to a tele-health appointment, or connect to a virtual hub for additional services. Similarly, a virtual hospital at home may involve patients checking-in with the call light, the virtual care coordinator 502 sensing messages to the patients, providing care resources, and facilitating patient care sessions.

The telehealth kiosk may involve the patient systems 206 including the peripheral devices 108. The patient initiates a patient care session using the call light on the patient device 106, and the virtual care coordinator 502 activates a patient care session or sends a message regarding status. The virtual care coordinator 502 transfers the patient to join the appropriate patient care session with the provider or handles the patient care session directly. The audio input and video input may be switched between to obtain patient medical data directly from the peripheral devices 108 and continue discussion with the patient.

The virtual care system may track various metrics associated with each patient. The metrics may be used for compliance with certain requirements, in some implementations. For example, if a patient has requested a visit, the virtual care system may track whether the visit was performed.

Turning to FIGS. 6-15 example interfaces of the virtual care interface 102 generated by the virtual care system 202 are illustrated. It will be appreciated that the various interfaces are exemplary only and not intended to be limiting. The interfaces may be presented using the various user devices 304, including the patient device 106, the patient systems 206, the virtual coordinator system 208, the provider system 210, and other computing devices.

Figure 6:
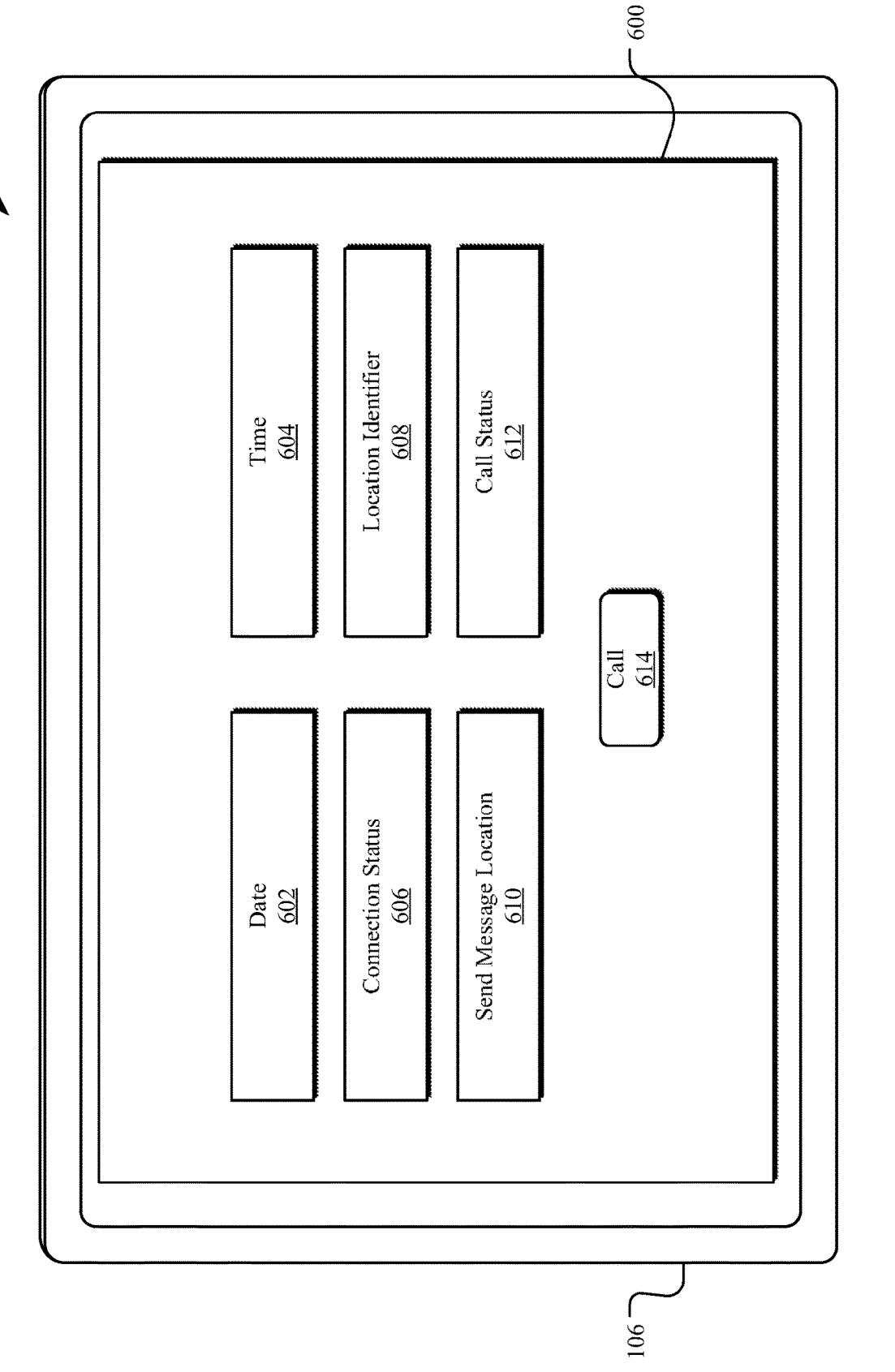
FIG. 6 shows an example patient interface in a locked state.

Referring first to FIG. 6, an example patient interface 600 is shown in a locked state. In one implementation, the patient interface 600 includes date 602, time 604, connection status 606, location identifier 608, send message location 610, call status 612, and a call light 614. The date 602 and time 604 may present the current date and time. The connection status 606 may provide an indication regarding whether the patient device 106 is connected to the virtual care system 202. The location identifier 608 presents the identifier associated with the patient, the patient room, or the patient device 106 for joining patient care sessions. The send message location 610 presents messages from other users and in some cases permits messages to be sent in reply to users or directly to the virtual care coordinator 502. The call status 612 indicates whether the call light 614 is activated or a patient care session in the form of patient monitoring is active. The call light 614 may be used to reach the virtual care coordinator 502.

Figure 7:
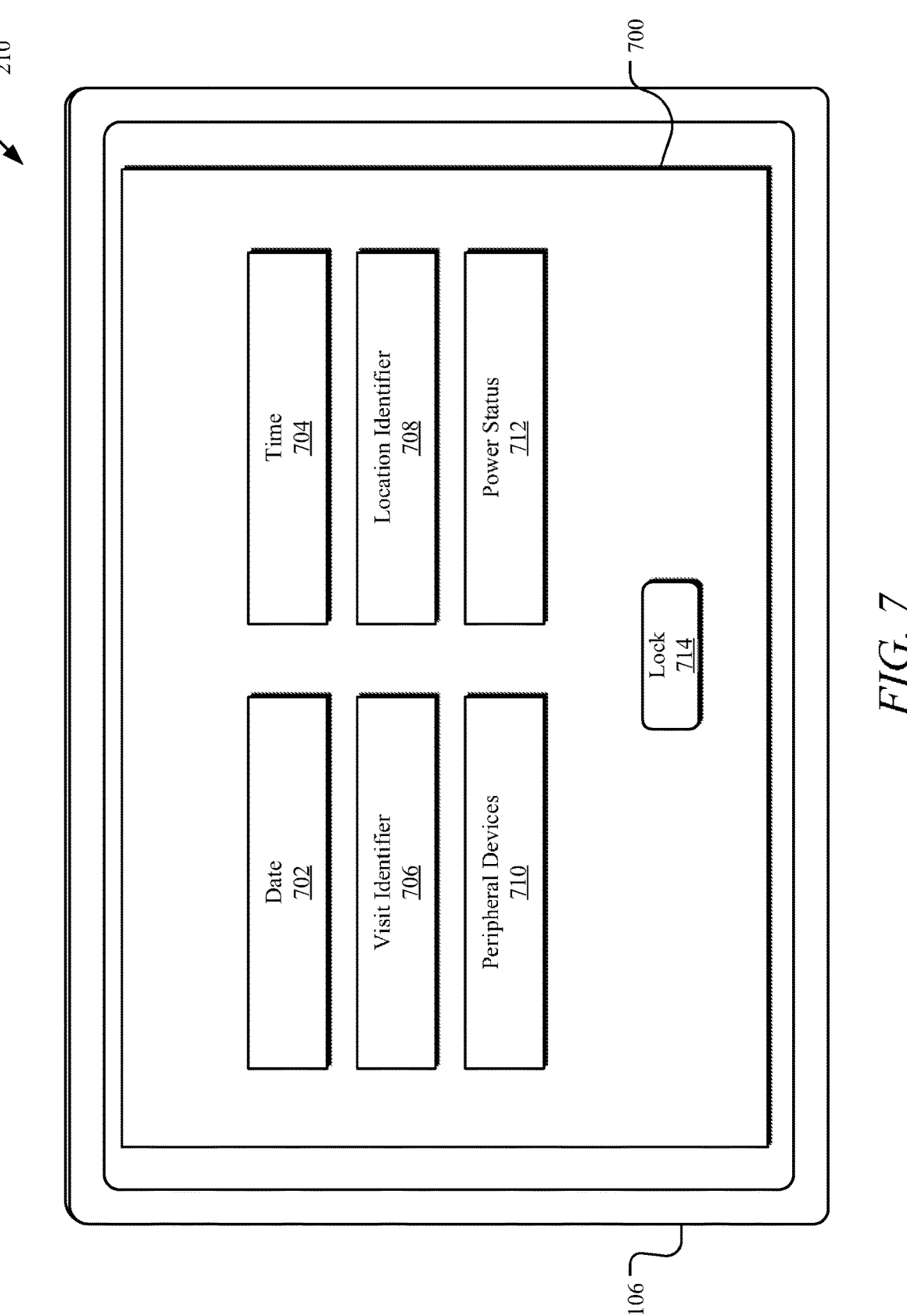
FIG. 7 depicts an example patient interface in an unlocked state.

FIG. 7 depicts an example patient interface 700 in an unlocked state. In one implementation, the patient interface 700 includes date 702, time 704, visit identifier 706, location identifier 708, peripheral devices 710, power status 712, and a lock option 714. The date 702 and time 704 may present the current date and time. The visit identifier 706 corresponds to the virtual care coordinator 502 to automatically join patient care sessions with the virtual care coordinator 502. The location identifier 708 presents the identifier associated with the patient, the patient room, or the patient device 106 for joining patient care sessions. The peripheral devices 710 provides options and controls for configuring the peripheral devices 108. The power status 712 indicates a power level of the patient device 106. The lock option 714 may be used to transition into the locked state to prevent or otherwise restrict patient access.

Figure 8:
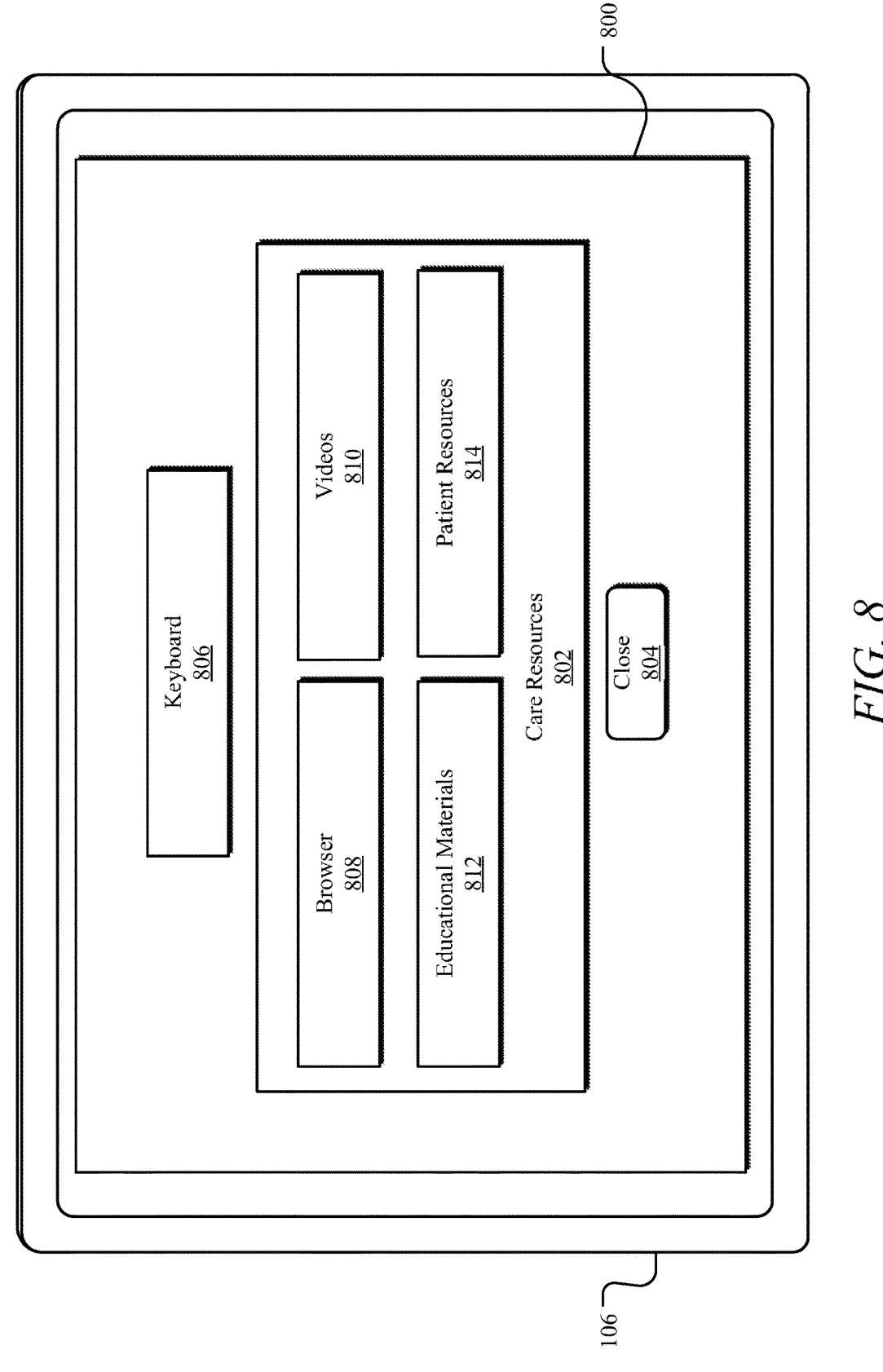
FIG. 8 depicts an example patient resource interface.

FIG. 8 depicts an example patient resource interface 800. In one implementation, the patient resource interface 800 includes care resources 802, a close option 804, and a graphical keyboard 806. The care resources 802 may include a browser 808, videos 810, educational materials 812, and patient resources 814. The browser 808 may be limited to navigation to designated websites. The videos 810 may similarly include designated videos that may be played, which may be streamed from online or stored locally.

Figure 9:
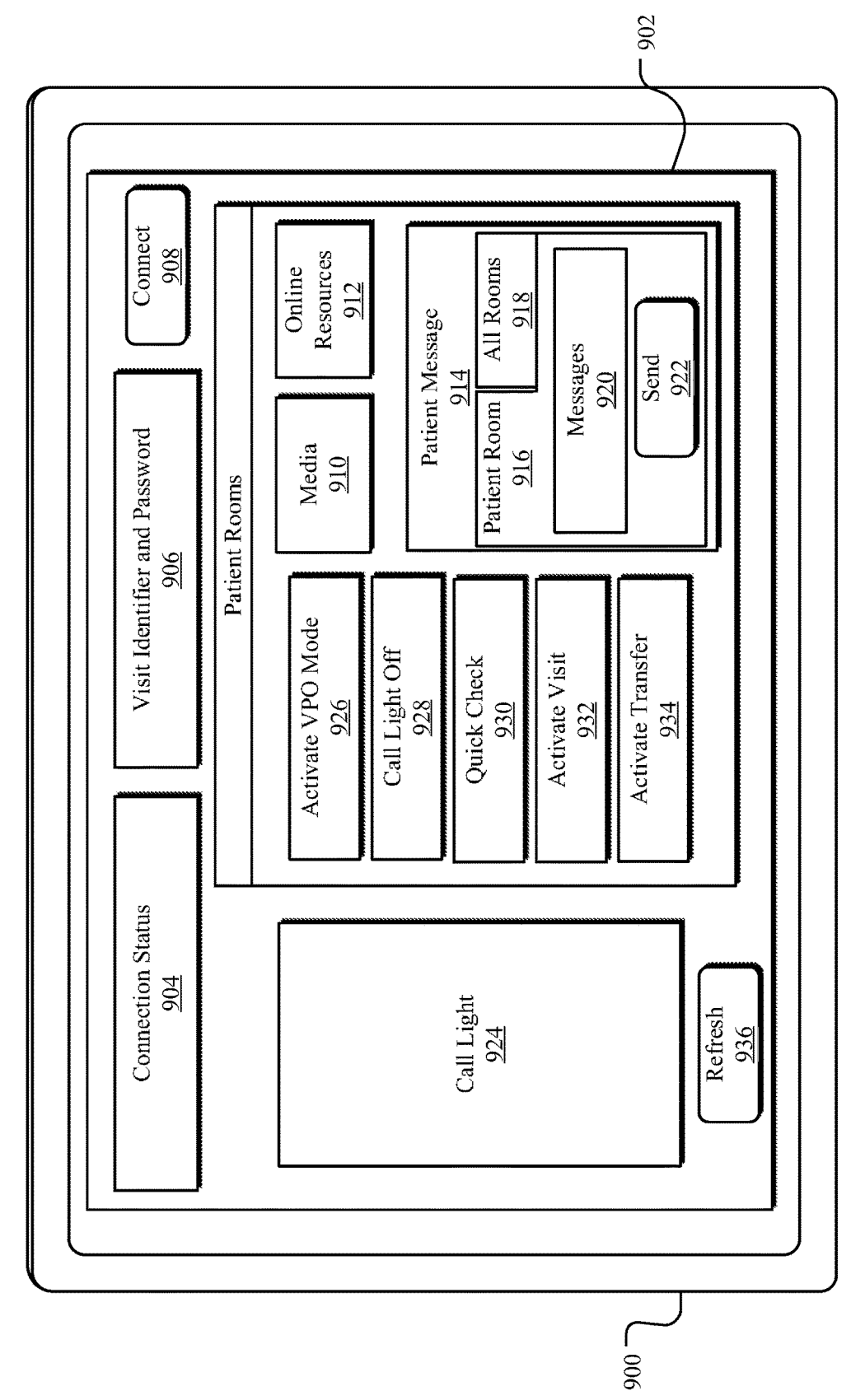
FIG. 9 shows an example virtual care coordinator interface.

FIG. 9 shows an example virtual care coordinator interface 902 displayed on the user device 304, such as a coordinator device 900 of the virtual coordinator system 208. In one implementation, the virtual care coordinator interface 902 includes a connection status 904, a visit identifier and password 906, a connection option 908, media 910, online resources 912, patient messaging 914, an activate virtual patient observation mode option 926, a call light section 924, a call light off option 928, an activate visit option 932, an activate transfer option 934, and a refresh option 936. The patient messaging 914 may include tabs for sending messages to select patient rooms 916 and all rooms 918, along with a message content section 920, and a message send option 922.

The visit identifier and password 906 facilitates input of the patient identifier associated with a particular patient, patient room, and/or the patient device 106 for initiating a patient care session. The connect option 908 initiates the patient care session accordingly. The media 910 may include a set of available care resources, such as videos and the online resources 912 to provide to the patient. The media 910 may include a drop down of available videos that may be selected with a play video option. The online resources 912 may include a drop down of available web resources, a navigate to webpage option, and a hide browser option.

The activate virtual patient observation mode option 926 may be used to initiate virtual patient monitoring with one or more patients. The call light section 924 lists the patient devices or patient rooms which have a triggered call light. Using the call light section 924, a particular patient device may be selected and the call light off option 928, the activate visit option 932, or the activate transfer option 934 may be used. The call light off option 928 turns the call light off for the selected patient devices. The activate visit option 932 may be used to perform a quick check on the patient or to initiate a patient care session. The quick check may be used to view a patient without disrupting the locked state of the virtual care interface 102 or to initiate the media 910 or online resources 912 on the virtual care interface 102 for the patient. The activate transfer option 934 may be used to transfer the patient device to another patient care session. The refresh option 936 may be used to refresh the call light section 924, which may also automatically refresh at regular intervals.

Figure 10:
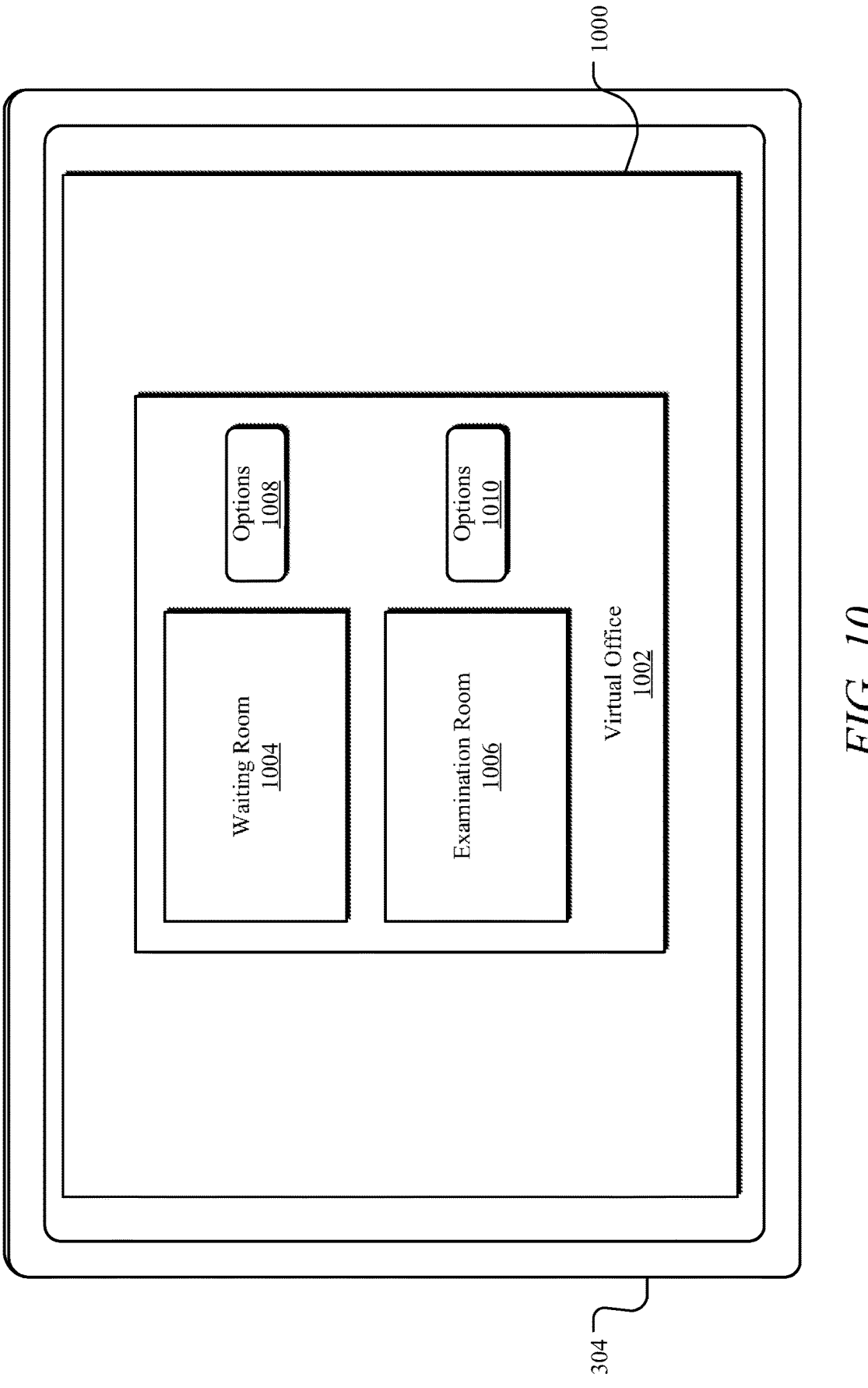
FIG. 10 illustrates an example visit coordination interface.

FIG. 10 illustrates an example visit coordination interface 1000. In one implementation, the visit coordination interface 1000 includes a virtual office 1002 with a waiting room 1004, and an examination room 1006, as well as options 1008 and 1010 associated with each. The visit coordination interface 1000 may be presented when the activate visit option 932 is selected or a patient care session is otherwise initiated. Prior to joining the patient device in the patient care session in the examination room 1006, the patient device may be directed to the waiting room 1004. Additionally, consent may be obtained from the patient prior to initiating the patient care session and joining the patient device in the examination room 1006.

Figure 11:
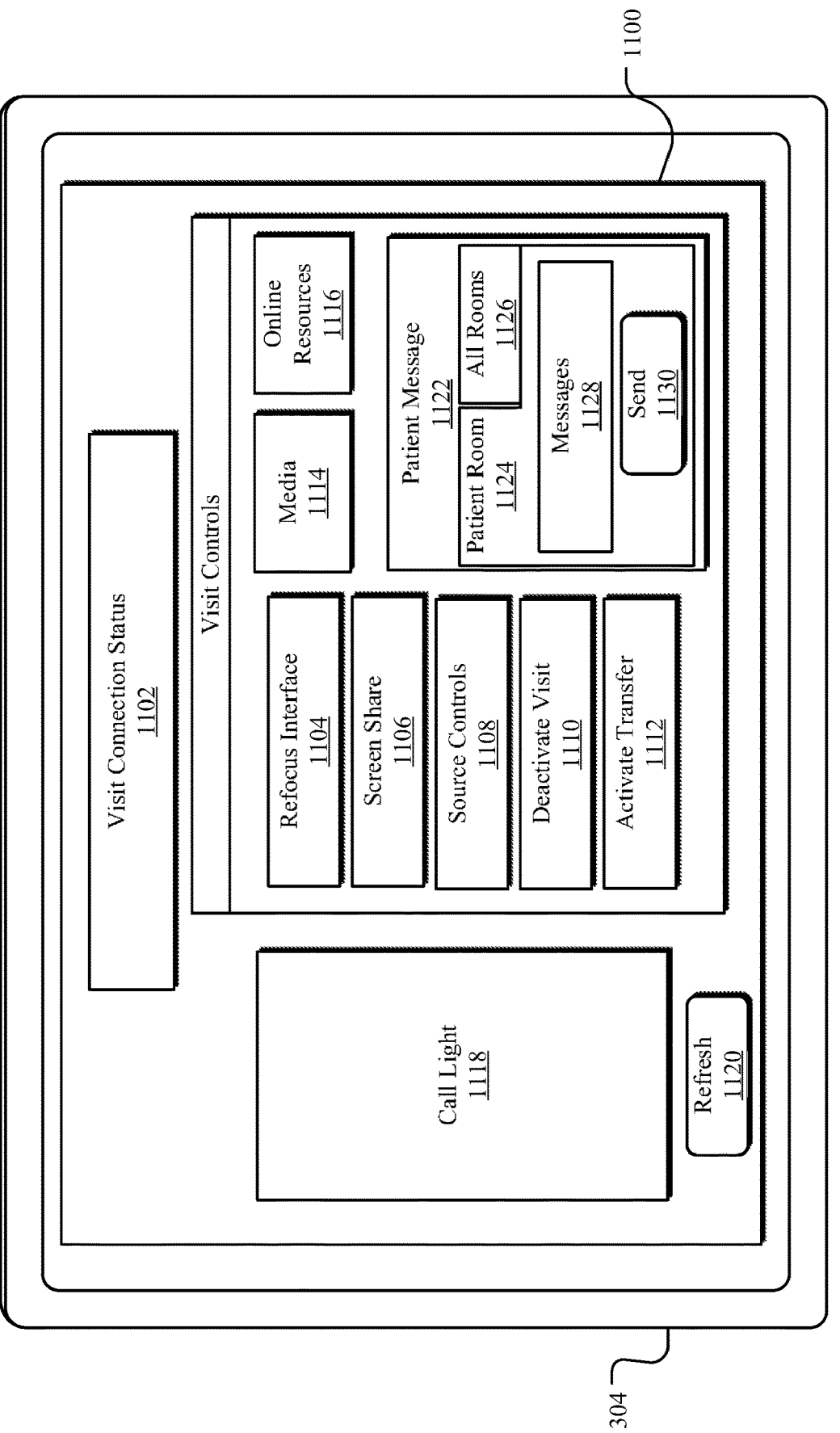
FIG. 11 shows an example patient visit interface.

FIG. 11 shows an example patient visit interface 1100. In one implementation, the patient visit interface 1100 includes a visit connection status 1102, and visit controls. The visit controls include, without limitation, a refocus interface option 1104, a screen share option 1106, source controls 1108, a deactivate visit option 1110, an activate transfer option 1112, media controls 1114, online resources controls 1116, a call light section 1118, a refresh option 1120, and patient messaging controls 1122. The patient messaging controls 1122 may include tabs for sending messages to select patient rooms 1124 and all rooms 1126, along with a message content section 1128, and a message send option 1130. The refocus interface option 1104 may be used to refocus the virtual care interface 102 or the capture of audio or video input. The source controls 1108 may be used to change the audio input and the video input, for example between the patient device 106 and the peripheral devices 108. The deactivate visit option 1110 ends the patient care session, and the activate transfer option 1112 transfers users to other patient care sessions.

Figure 12:
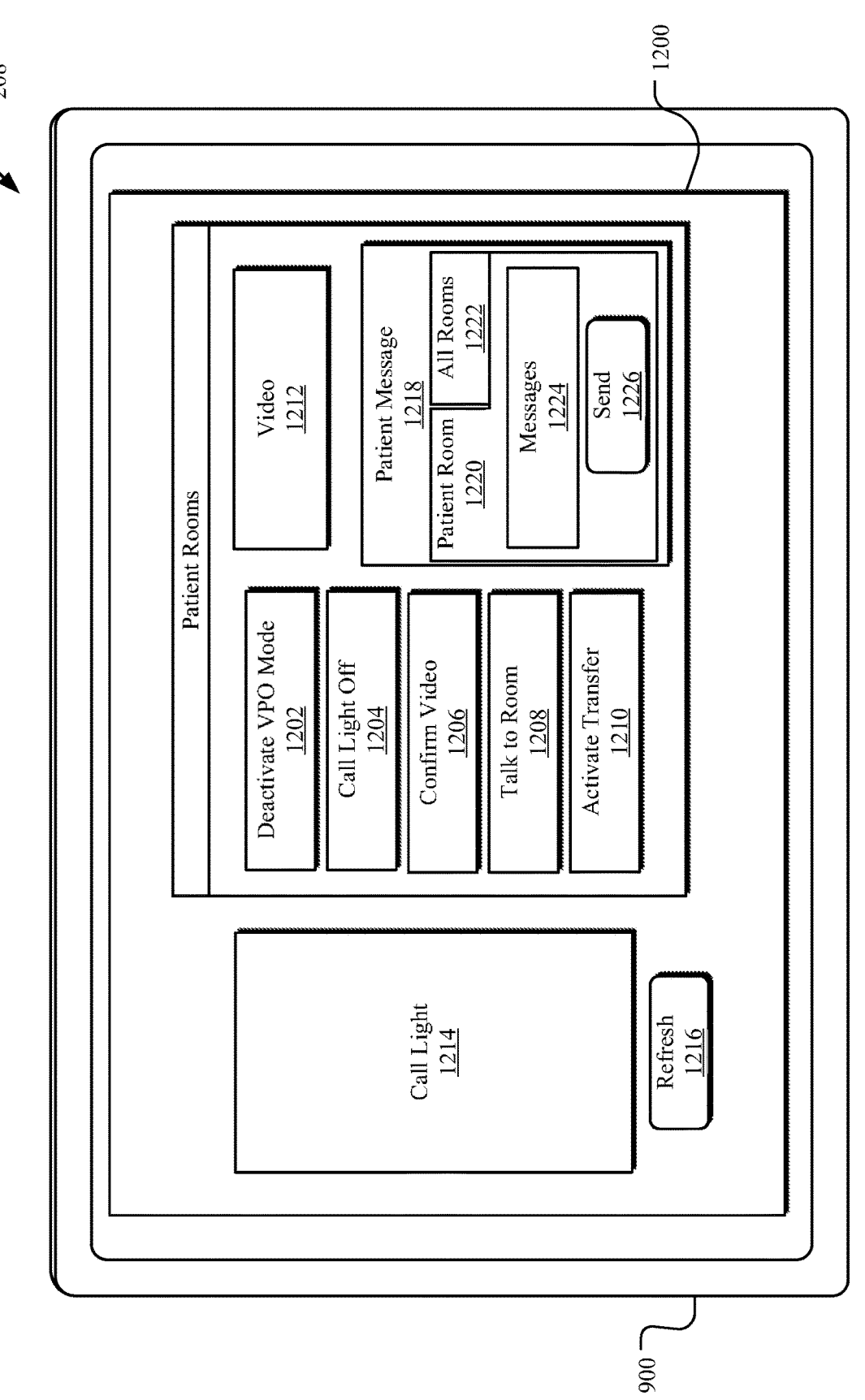
FIG. 12 depicts an example patient monitor interface.

Turning to FIG. 12, an example patient monitor interface 1200 in connection with virtual patient observation is shown. In one implementation, the patient monitor interface 1200 includes a deactivate virtual patient observation mode option 1202, a call light off option 1204, a confirm video option 1206, a talk to room option 1208, an activate transfer option 1210, a video option 1212, a call light section 1214, a refresh option 1216, and patient messaging 1218. The patient messaging 1218 may include tabs for sending messages to select patient rooms 1220 and all rooms 1222, along with a message content section 1224, and a message send option 1226. The patient monitor interface 1200 may be presented when the activate virtual patient observation mode option 926 is selected. The confirm video option 1206 may be used to confirm patient consent for the virtual patient observation, and the video option 1212 may be used to control video, such as initiating video observation. The deactivate virtual patient observation mode option 1202 may be used to deactivate the virtual patient observation. The talk to room option 1208 may be used to interact with one of the rooms independently, which will unmute the corresponding patient device while maintaining the other rooms on mute, as described herein. The talk to room option 1208 may similarly be used to stop interacting with the room and put the speakers of the room on mute and unmute the microphones of the other rooms.

Figure 13:
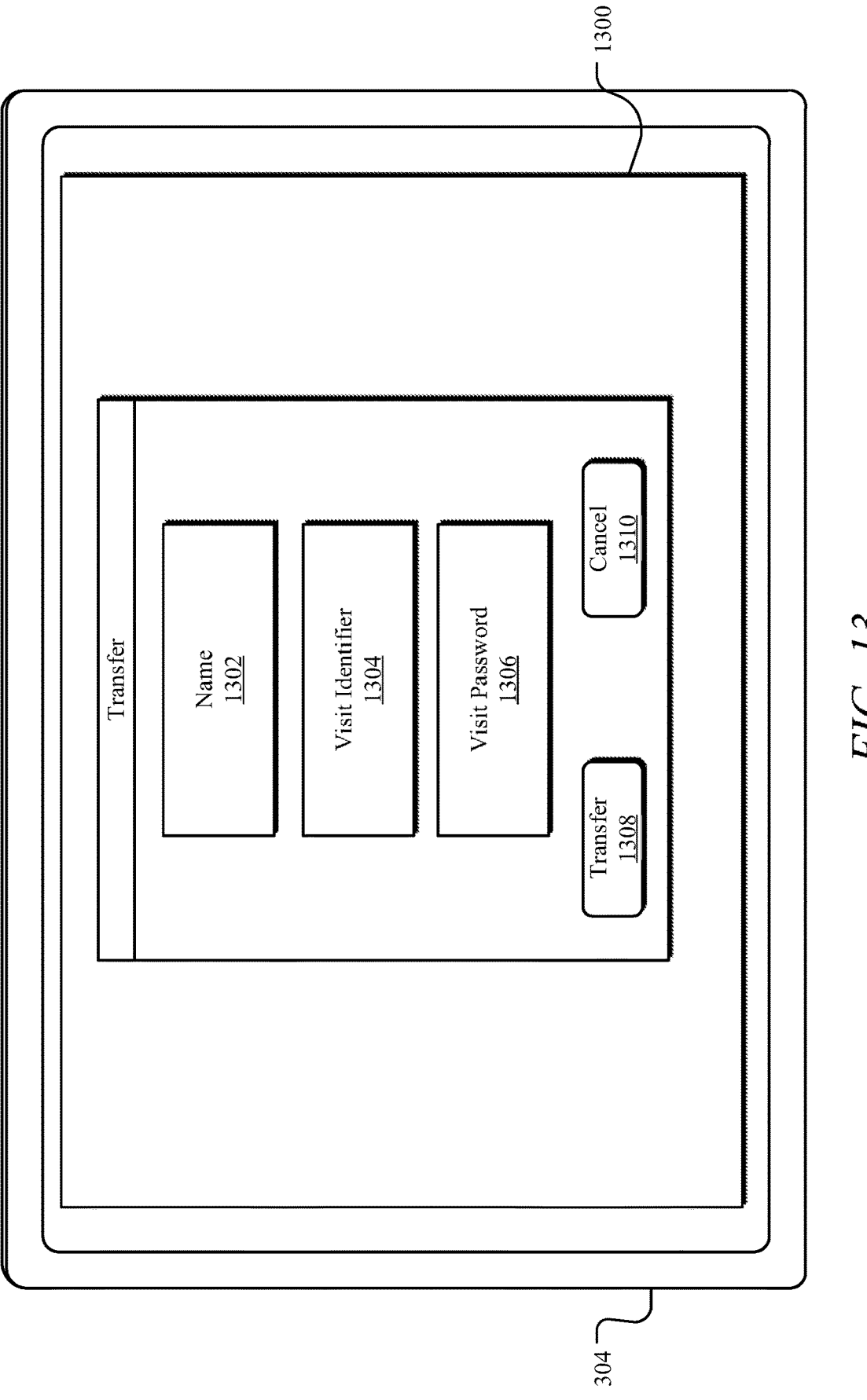
FIG. 13 shows an example transfer interface.

FIG. 13 shows an example transfer interface 1300. In one implementation, the transfer interface 1300 includes a name 1302, a visit identifier 1304, a visit password 1306, a transfer option 1308, and a cancel option 1310. The transfer interface 1300 may be presented upon selection of the activate transfer option. The transfer interface 1300 may facilitate transfer of the patient device to another existing patient care session. The virtual care system 202 automatically detects whether that patient care session is active at regular intervals (e.g., one minute). If the patient care session has ended, the transfer interface 1300 closes.

Figure 14:
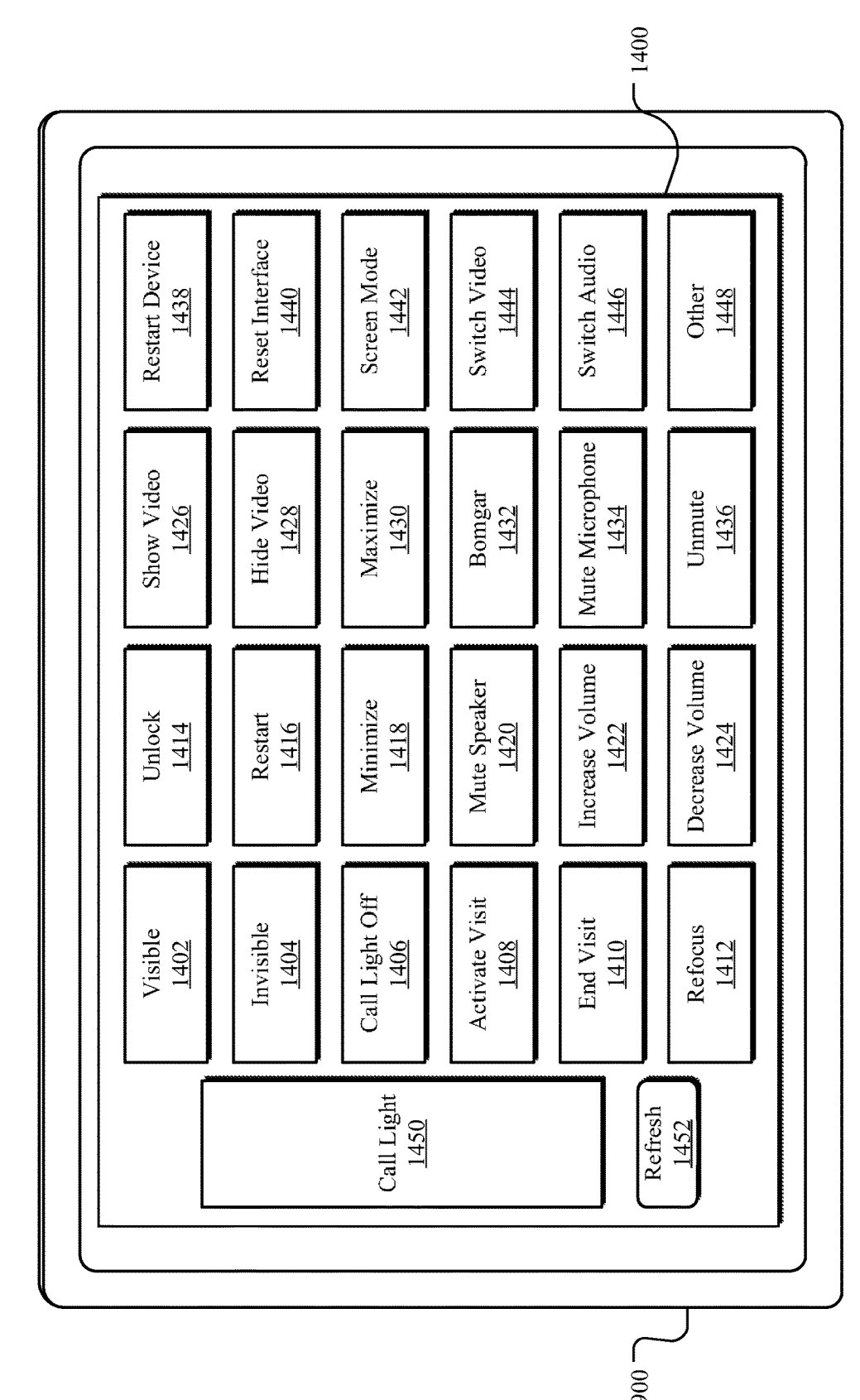
FIG. 14 illustrates an example virtual care command interface.

Referring to FIG. 14, an example virtual care command interface 1400 with various controls is shown. In one implementation, the virtual care command interface 1400 includes a visible option 1402, an invisible option 1404, a call light off option 1406, an activate visit option 1048, an end visit option 1410, a refocus option 1412, an unlock option 1414, a restart option 1416, a minimize option 1418, a mute speaker option 1420, an increase volume option 1422, a decrease volume option 1424, a show video option 1426, a hide video option 1428, a maximize option 1430, a bomgar option 1432, a mute microphone option 1434, an unmute microphone option 1436, a restart device option 1438, a reset interface 1440, a screen mode option 1442, a switch video input option 1444, a switch audio input option 1446, other options 1448, a call light section 1450, and a refresh option 1452.

Figure 15:
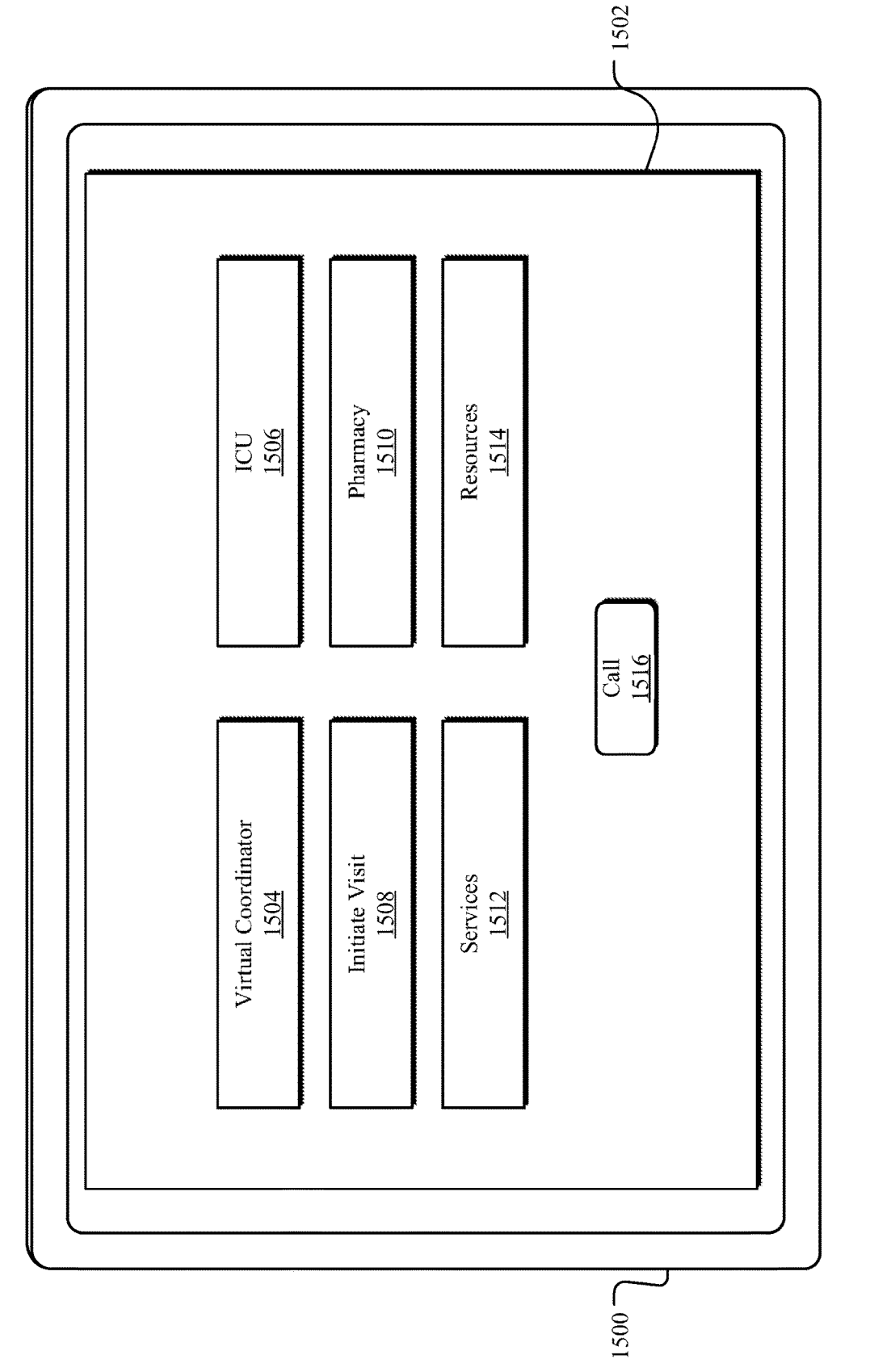
FIG. 15 shows an example provider interface.

FIG. 15 shows an example provider interface 1502 displayed on the user device 304, such as a provider device 1500 of the provider system 210. In one implementation, the provider interface 1502 includes a virtual coordinator option 1504, an ICU option 1506, an initiate visit option 1508, a pharmacy option 1510, a services option 1512, a resources option 1514, and a call light 1516. The options 1504-1516 may be used to access various resources or join a patient care session with corresponding personnel.

Figure 16:
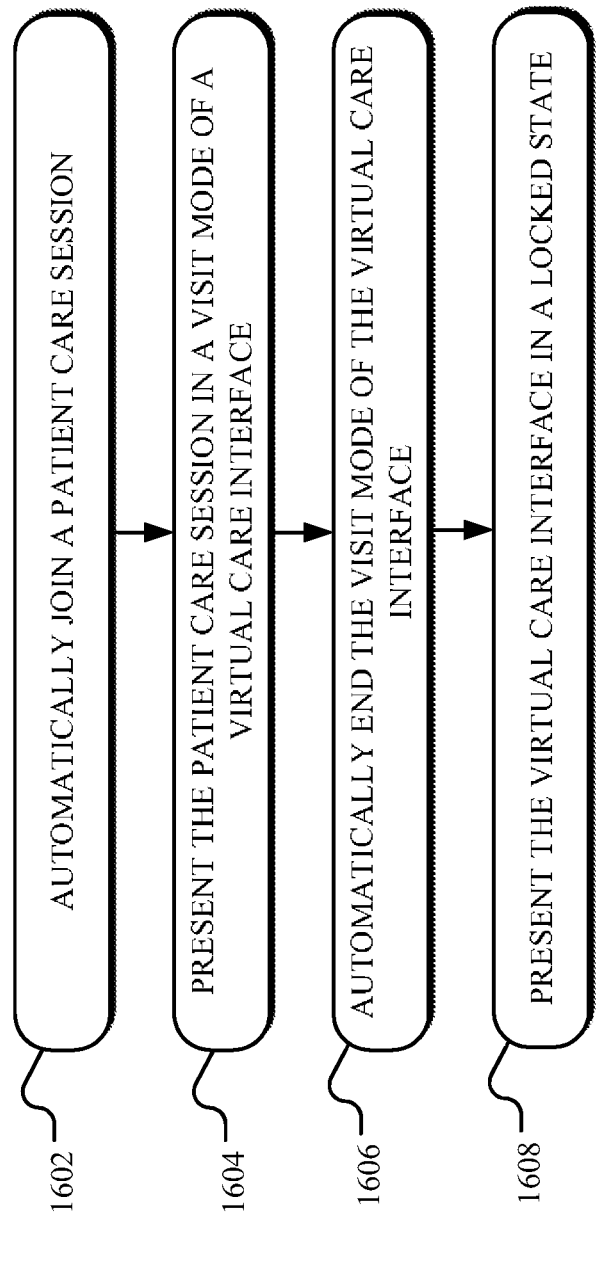
FIG. 16 illustrates example operations for providing virtual care for a patient.

Referring to FIG. 16 example operations 1600 for providing virtual care for a patient are illustrated. In one implementation, an operation 1602 automatically joins a patient care session corresponding to care for the patient in response to a command to initiate the patient care session. The patient care session may be automatically joined using a location identifier and a password that are automatically obtained. An operation 1604 presents the patient care session in a visit mode of a virtual care interface. The visit mode prevents access to functionality outside of the patient care session. An operation 1606 automatically ends the visit mode of the virtual care interface following a termination of the patient care session, and an operation 1608 presents the virtual care interface in a locked state.

Figure 17:
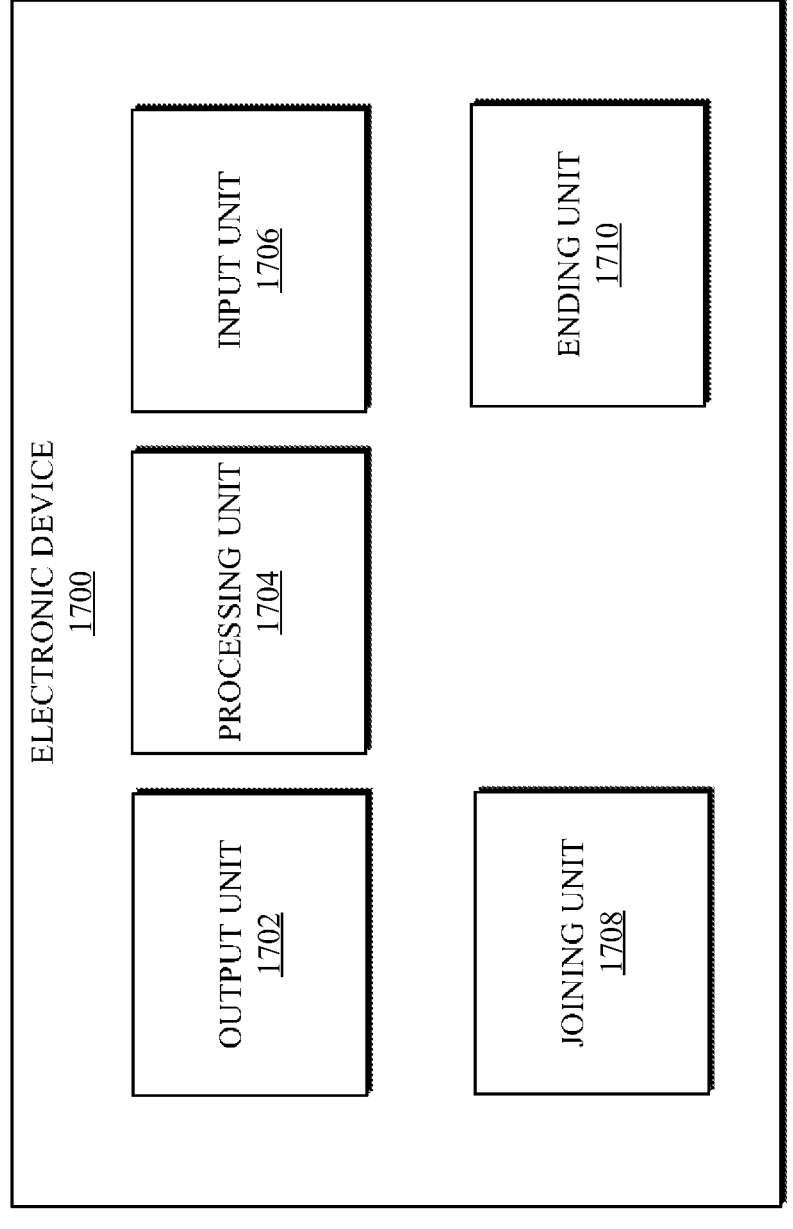
FIG. 17 illustrates an example electronic device including operational units arranged to perform various operations of the presently disclosed technology.

Turning to FIG. 17, an electronic device 1700 including operational units 1702-1710 arranged to perform various operations of the presently disclosed technology is shown. The operational units 1702-1710 of the device 1700 are implemented by hardware or a combination of hardware and software to carry out the principles of the present disclosure. It will be understood by persons of skill in the art that the operational units 1702-1710 described in FIG. 17 may be combined or separated into sub-blocks to implement the principles of the present disclosure. Therefore, the description herein supports any possible combination or separation or further definition of the operational units 1702-1710.

In one implementation, the electronic device 1700 includes an output unit 1702 configured to present information, such as the virtual care interface 102, using one or more output devices or systems and a processing unit 1704 in communication with the output unit 1702 and an input unit 1706 configured to receive data from one or more input devices or systems. Various operations described herein may be implemented by the processing unit 1704 using data received by the input unit 1706 to output information for presentation using the output unit 1702.

Additionally, in one implementation, the electronic device 1700 includes units implementing the operations described with respect to FIG. 16. For example, the operation 1602 may be implemented by a joining unit 1708, and the operation 1606 may be implemented by an ending unit 1710. The electronic device 1700 may include various other units each implementing one of the operations 1602-1608.

Figure 18:
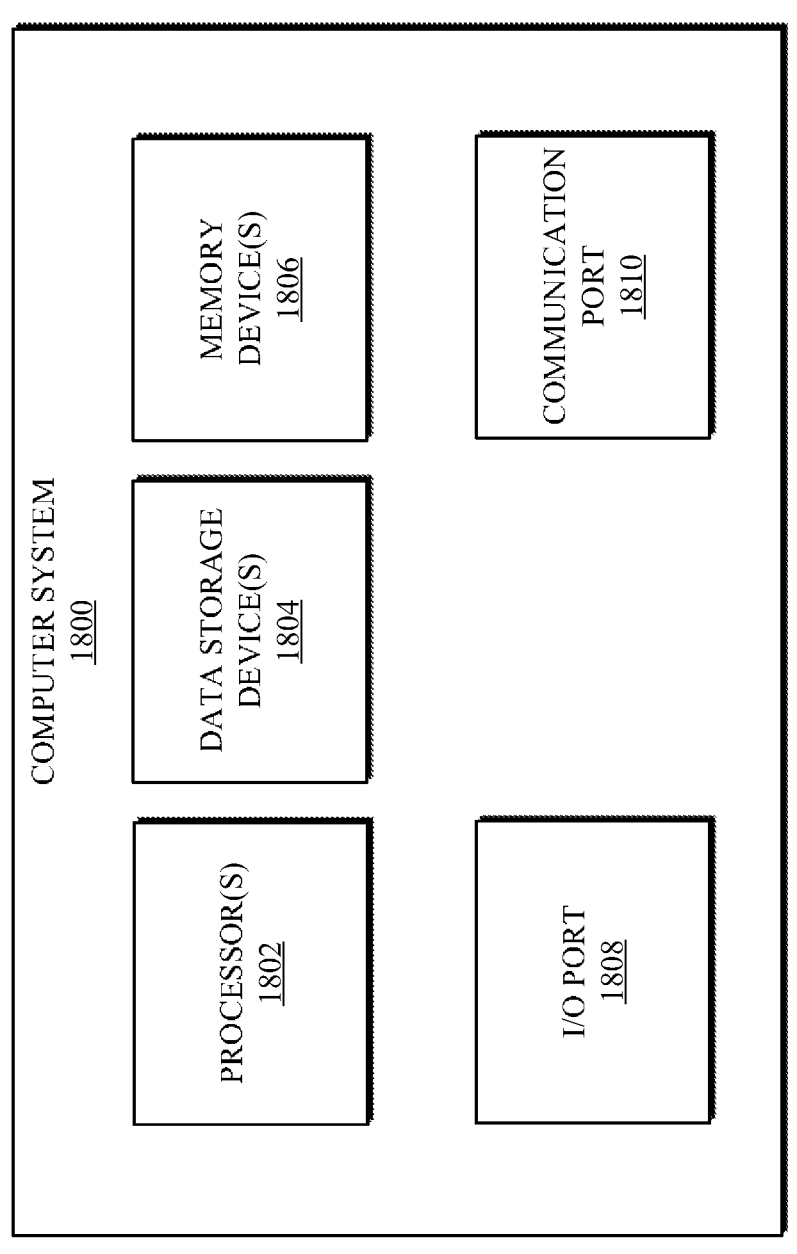
FIG. 18 shows an example computing system that may implement various systems and methods discussed herein.

Referring to FIG. 18, a detailed description of an example computing system 1800 having one or more computing units that may implement various systems and methods discussed herein is provided. The computing system 1800 may be applicable to the patient device 106, the peripheral devices 108, the patient systems 206, the virtual care system 208, the provider systems 210, the server 214, the user devices 304, the communications manager 308, and other computing or network devices described herein. It will be appreciated that specific implementations of these devices may be of differing possible specific computing architectures not all of which are specifically discussed herein but will be understood by those of ordinary skill in the art.

The computer system 1800 may be a computing system is capable of executing a computer program product to execute a computer process. Data and program files may be input to the computer system 1800, which reads the files and executes the programs therein. Some of the elements of the computer system 1800 are shown in FIG. 18, including one or more hardware processors 1802, one or more data storage devices 1804, one or more memory devices 1808, and/or one or more ports 1808-1810. Additionally, other elements that will be recognized by those skilled in the art may be included in the computing system 1800 but are not explicitly depicted in FIG. 18 or discussed further herein. Various elements of the computer system 1800 may communicate with one another by way of one or more communication buses, point-to-point communication paths, or other communication means not explicitly depicted in FIG. 18.

The processor 1802 may include, for example, a central processing unit (CPU), a microprocessor, a microcontroller, a digital signal processor (DSP), and/or one or more internal levels of cache. There may be one or more processors 1802, such that the processor 1802 comprises a single central-processing unit, or a plurality of processing units capable of executing instructions and performing operations in parallel with each other, commonly referred to as a parallel processing environment.

The computer system 1800 may be a conventional computer, a distributed computer, or any other type of computer, such as one or more external computers made available via a cloud computing architecture. The presently described technology is optionally implemented in software stored on the data stored device(s) 1804, stored on the memory device(s) 1806, and/or communicated via one or more of the ports 1808-1810, thereby transforming the computer system 1800 in FIG. 18 to a special purpose machine for implementing the operations described herein. Examples of the computer system 1800 include personal computers, terminals, workstations, mobile phones, tablets, laptops, personal computers, multimedia consoles, gaming consoles, set top boxes, and the like.

The one or more data storage devices 1804 may include any non-volatile data storage device capable of storing data generated or employed within the computing system 1800, such as computer executable instructions for performing a computer process, which may include instructions of both application programs and an operating system (OS) that manages the various components of the computing system 1800. The data storage devices 1804 may include, without limitation, magnetic disk drives, optical disk drives, solid state drives (SSDs), flash drives, and the like. The data storage devices 1804 may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory devices 1806 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in the data storage devices 1804 and/or the memory devices 1806, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

In some implementations, the computer system 1800 includes one or more ports, such as an input/output (I/O) port 1808 and a communication port 1810, for communicating with other computing, network, or vehicle devices. It will be appreciated that the ports 1808-1810 may be combined or separate and that more or fewer ports may be included in the computer system 1800.

The I/O port 1808 may be connected to an I/O device, or other device, by which information is input to or output from the computing system 1800. Such I/O devices may include, without limitation, one or more input devices, output devices, and/or environment transducer devices.

In one implementation, the input devices convert a human-generated signal, such as, human voice, physical movement, physical touch or pressure, and/or the like, into electrical signals as input data into the computing system 1800 via the I/O port 1808. Similarly, the output devices may convert electrical signals received from computing system 1800 via the I/O port 1808 into signals that may be sensed as output by a human, such as sound, light, and/or touch. The input device may be an alphanumeric input device, including alphanumeric and other keys for communicating information and/or command selections to the processor 1802 via the I/O port 1808. The input device may be another type of user input device including, but not limited to: direction and selection control devices, such as a mouse, a trackball, cursor direction keys, a joystick, and/or a wheel; one or more sensors, such as a camera, a microphone, a positional sensor, an orientation sensor, a gravitational sensor, an inertial sensor, and/or an accelerometer; and/or a touch-sensitive display screen ("touchscreen"). The output devices may include, without limitation, a display, a touchscreen, a speaker, a tactile and/or haptic output device, and/or the like. In some implementations, the input device and the output device may be the same device, for example, in the case of a touchscreen.

The environment transducer devices convert one form of energy or signal into another for input into or output from the computing system 1800 via the I/O port 1808. For example, an electrical signal generated within the computing system 1800 may be converted to another type of signal, and/or vice-versa. In one implementation, the environment transducer devices sense characteristics or aspects of an environment local to or remote from the computing device 1800, such as, light, sound, temperature, pressure, magnetic field, electric field, chemical properties, physical movement, orientation, acceleration, gravity, and/or the like. Further, the environment transducer devices may generate signals to impose some effect on the environment either local to or remote from the example computing device 1800, such as, physical movement of some object (e.g., a mechanical actuator), heating or cooling of a substance, adding a chemical substance, and/or the like.

In one implementation, a communication port 1810 is connected to a network by way of which the computer system 1800 may receive network data useful in executing the methods and systems set out herein as well as transmitting information and network configuration changes determined thereby. Stated differently, the communication port 1810 connects the computer system 1800 to one or more communication interface devices configured to transmit and/or receive information between the computing system 1800 and other devices by way of one or more wired or wireless communication networks or connections. Examples of such networks or connections include, without limitation, Universal Serial Bus (USB), Ethernet, Wi-Fi, Bluetooth®, Near Field Communication (NFC), Long-Term Evolution (LTE), and so on. One or more such communication interface devices may be utilized via the communication port 1810 to communicate one or more other machines, either directly over a point-to-point communication path, over a wide area network (WAN) (e.g., the Internet), over a local area network (LAN), over a cellular (e.g., third generation (3G) or fourth generation (4G) or fifth generation (5G)) network or over another communication means. Further, the communication port 1810 may communicate with an antenna or other link for electromagnetic signal transmission and/or reception.

In an example implementation, patient care data, patient medical data, provider data, patient care session information, and software and other modules and services may be embodied by instructions stored on the data storage devices 1804 and/or the memory devices 1806 and executed by the processor 1802.

The system set forth in FIG. 18 is but one possible example of a computer system that may employ or be configured in accordance with aspects of the present disclosure. It will be appreciated that other non-transitory tangible computer-readable storage media storing computer-executable instructions for implementing the presently disclosed technology on a computing system may be utilized.

In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to, magnetic storage medium, optical storage medium; magneto-optical storage medium, read only memory (ROM); random access memory (RAM); erasable programmable memory (e.g., EPROM and EEPROM); flash memory; or other types of medium suitable for storing electronic instructions.

While the present disclosure has been described with reference to various implementations, it will be understood that these implementations are illustrative and that the scope of the present disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. One or more tangible non-transitory computer-readable storage media storing computer-executable instructions for performing a computer process on a computing system, the computer process comprising:

presenting, by a patient device, a virtual care interface in a locked state, the locked state being controlled by an access restriction system of the virtual care system, the virtual care interface being presented, in the locked state, as a continuous layer across an entirety of a display of the patient device and intercepting input captured using one or more input devices of the patient device to prevent access to other systems and functions of the patient device outside of the virtual care interface;

automatically joining a patient care session within the virtual care interface corresponding to care for a patient in response to a command to initiate the patient care session, the patient care session being automatically joined using a location identifier and a password and without user interaction with the virtual care interface at the patient device;

transitioning the virtual care interface from the locked state into a visit mode, the visit mode preventing access to functionality outside of the patient care session by presenting the virtual care interface as the continuous layer that becomes transparent to present the patient care session while continuing to intercept input uncorrelated with the patient care session;

presenting the patient care session in the visit mode, the access restriction system rejecting input corresponding to functionality outside of the patient care session;

periodically querying, across a predetermined interval, a state of the virtual care interface, the state of the virtual care interface indicating whether the patient care session is ongoing, wherein periodically querying comprises detecting, at the predetermined interval, whether a video conferencing application associated with the patient care session is running via the virtual care interface;

automatically ending the visit mode of the virtual care interface following return of the queried state indicating a termination of the patient care session;

transitioning the virtual care interface into the locked state; and presenting the virtual care interface in the locked state, the access restriction system permitting access to functionality corresponding to the locked state.

2. The one or more tangible non-transitory computer-readable storage media of claim 1, wherein the locked state includes a call light and a messaging display.

3. The one or more tangible non-transitory computer-readable storage media of claim 1, wherein the virtual care interface is transitioned from the locked state to an unlocked state in response to an authenticated command.

4. The one or more tangible non-transitory computer-readable storage media of claim 1, wherein the command to initiate the patient care session is issued using a virtual coordinator system.

5. The one or more tangible non-transitory computer-readable storage media of claim 1, wherein the patient care session includes a patient examination using one or more peripheral devices.

6. The one or more tangible non-transitory computer-readable storage media of claim 5, wherein the virtual care interface switches between a plurality of input sources, the plurality of input sources corresponding to the one or more peripheral devices and a patient device.

7. The one or more tangible non-transitory computer-readable storage media of claim 1, wherein the patient care session includes an observation session, the observation session including real time observation of the patient among a plurality of patients, the observation session including the virtual care interface being in an observation mode.

8. The one or more tangible non-transitory computer-readable storage media of claim 7, further comprising:

preventing the plurality of patients from seeing or hearing each other in the observation mode.

9. The one or more tangible non-transitory computer-readable storage media of claim 1, further comprising:

joining a waiting room associated with the patient care session prior to automatically joining the patient care session.

10. A method for providing virtual care for a patient, the method comprising:

presenting a virtual care interface in a locked state on a patient device, the locked state being controlled by an access restriction system configured to prevent access to functionality of the patient device outside of the virtual care interface in the locked state;

automatically joining a patient care session within the virtual care interface corresponding to care for the patient in response to a command to initiate the patient care session, the patient care session being automatically joined with a patient device using a location identifier and a password;

transitioning the virtual care interface from the locked state into a visit mode, the visit mode preventing access to functionality of the patient device outside of the patient care session;

presenting the patient care session in the visit mode, the access restriction system rejecting input corresponding to functionality outside of the patient care session;

periodically querying, across a predetermined interval, a state of the virtual care interface, the state of the virtual care interface indicating whether the patient care session is ongoing;

automatically ending the visit mode of the virtual care interface following return of the queried state indicating a termination of the patient care session;

transitioning the virtual care interface into the locked state; and presenting the virtual care interface in the locked state using the patient device, the access restriction system permitting access to functionality corresponding to the locked state.

11. The method of claim 10, wherein the locked state includes a call light and a messaging display.

12. The method of claim 10, wherein the virtual care interface is transitioned from the locked state to an unlocked state in response to an authenticated command.

13. The method of claim 10, wherein the command to initiate the patient care session is issued using a virtual coordinator system.

14. The method of claim 10, wherein the patient care session includes a patient examination using one or more peripheral devices.

15. The method of claim 14, wherein the virtual care interface switches between a plurality of input sources, the plurality of input sources corresponding to the one or more peripheral devices and the patient device.

16. The method of claim 10, wherein the patient care session includes an observation session, the observation session including real time observation of the patient among a plurality of patients, the observation session including the virtual care interface being in an observation mode.

17. The method of claim 16, further comprising:

preventing the plurality of patients from seeing or hearing each other in the observation mode.

18. The method of claim 10, further comprising:

joining a waiting room associated with the patient care session prior to automatically joining the patient care session.

19. A system for providing virtual care for a patient, the system comprising:

a virtual coordinator system configured to issue a command for initiating a patient care session corresponding to care for the patient;

a patient device configured to present a virtual care interface in a locked state, the locked state being controlled by an access restriction system configured to prevent access to functionality of the patient device outside of the virtual care interface in the locked state, automatically join the patient care session within the virtual care interface in response to the command to initiate the patient care session, the patient care session being automatically joined using a location identifier and a password, the patient device transitioning the virtual care interface from the locked state into a visit mode, the visit mode preventing access to functionality outside of the patient care session, the patient device presenting the patient care session in the visit mode, the access restriction system rejecting input corresponding to functionality outside of the patient care session; and one or more provider devices configured to automatically join the patient care session in response to the command to initiate the patient care session, wherein the access restriction system is configured to periodically query, across a predetermined interval, a state of the virtual care interface, the state of the virtual care interface indicating whether the patient care session is ongoing, and automatically transition the virtual care interface from the visit mode into the locked state following return of the queried state indicating a termination of the patient care session.

20. The system of claim 19, further comprising:

one or more peripheral devices configured to capture patient medical data for presentation during the patient care session.

* * * * *